US012703885B2

(12) United States Patent
Loibl et al.

(10) Patent No.: US 12,703,885 B2
(45) Date of Patent: Aug. 11, 2026

(54) METHOD FOR PREDICTING THE RESPONSE TO CDK4/6 INHIBITOR THERAPY IN CANCER PATIENTS

(71) Applicant: GBG FORSCHUNGS GMBH, Neu-Isenburg (DE)

(72) Inventors: Sibylle Loibl, Neu-Isenburg (DE); Karsten Weber, Dreieich (DE); Baerbel Felder, Grasellenbach (DE)

(73) Assignee: GBG FORSCHUNGS GMBH, Neu-Isenburg (DE)

( * ) Notice: Subject to any disclaimer, the term of this patent is extended or adjusted under 35 U.S.C. 154(b) by 462 days.

(21) Appl. No.: 18/261,329

(22) PCT Filed: Jan. 17, 2022

(86) PCT No.: PCT/EP2022/050876

§ 371 (c)(1),
(2) Date: Jul. 13, 2023

(87) PCT Pub. No.: WO2022/152899

PCT Pub. Date: Jul. 21, 2022

(65) Prior Publication Data

US 2024/0093301 A1 Mar. 21, 2024

(30) Foreign Application Priority Data

Jan. 18, 2021 (EP) .................................... 21152186

(51) Int. Cl.
*C12Q 1/68* (2018.01)
*C12Q 1/6886* (2018.01)

(52) U.S. Cl.
CPC ..... *C12Q 1/6886* (2013.01); *C12Q 2600/106* (2013.01); *C12Q 2600/158* (2013.01)

(58) Field of Classification Search
CPC ....................................................... C12Q 1/68
See application file for complete search history.

(56) References Cited

U.S. PATENT DOCUMENTS

2016/0222458 A1* 8/2016 Miller .................... G16B 25/20
2022/0143022 A1* 5/2022 Hassig ................... A61K 31/17

FOREIGN PATENT DOCUMENTS

WO 2014172479 A1 10/2014
WO WO-2018183921 A1 * 10/2018 ........... C12Q 1/6886
WO WO-2019070755 A1 * 4/2019 ............. G16B 20/00

OTHER PUBLICATIONS

Sammons et al, HR+, HER2-Advanced Breast Cancer and CDK4/6 Inhibitors: Mode of Action, Clinical Activity, and Safety Profiles, Curr Cancer Drug Targets. 2017;17(7):637-649.*

(Continued)

*Primary Examiner* — Aaron A Priest
(74) *Attorney, Agent, or Firm* — McBee Moore & Vanik IP, LLC

(57) ABSTRACT

The present invention relates to a method for predicting a response or resistance to and/or a benefit from treatment with an inhibitor of cyclin-dependent kinases 4 (CDK4/6 inhibitor) in a subject suffering from a neoplastic disease, particularly breast cancer, comprising the step of: determining in a sample obtained from said subject the expression level of at least one marker selected from the group consisting of PD-L1, PIAS2, MAP2K6, DSG3, ABCC12, IFT52, ABCB6, ABCC1, ABCA5, ABCC6, ABCC11, CHUK, SUMO1, TDG, AURKA, SMC3, IKBKG and XPC, wherein the expression level of the at least one marker is indicative for predicting the response or resistance to and/or the benefit from the treatment with the CDK4/6 inhibitor in said subject. The invention further pertains to a CDK4/6 inhibitor for use in the treatment of neoplastic disease, particularly breast cancer, in a subject, wherein the subject has been determined to have a benefit from treatment with a CDK4/6 inhibitor in a method of the invention.

14 Claims, 5 Drawing Sheets

(56) References Cited

OTHER PUBLICATIONS

Bae, et al; "pl6 methylation is a potential predictive marker for abemaciclib sensitivity in gastric cancer", Biochemical Pharmacology, vol. 183, 114320 (Nov. 6, 2020 ).
Conklin; "Identification of Genomic Predictors of Response to the CDK4/6 Inhibitor Palbociclib using the UCLATORL Panel of Human Cancer Cell Lines", UCLA Electronic Theses and Dissertations (Jan. 1, 2013).
Del Re, et al; "Overexpression of TKI and CDK9 in plasma-derived exosomes is associated with clinical resistance to CDK4/6 inhibitors in metastatic breast cancer patients", Breast Cancer Research and Treatment, vol. 178, No. 1, pp. 57-62 (Jul. 26, 2019).
Finn, et al: "Biomarker Analyses of Response to Cyclin-Dependent Kinase 4/6 Inhibition and Endocrine Therapy in Women with Treatment-Naive Metastatic Breast Cancer", Clinical Cancer Research, vol. 26, No. 1, pp. 110-121 (Sep. 16, 2019).
International Search Report/Written Opinion issued in International Application No. PCT/EP2022/050876 (Jun. 23, 2022).
Mccartney, et al; "Mechanisms of Resistance to CDK4/6 Inhibitors: Potential Implications and Biomarkers for Clinical Practice", Frontiers in Oncology; vol. 9 (Jul. 23, 2019).
Migliaccio, et al; "CDK4/6 inhibitors: A focus on biomarkers of response and post-treatment therapeutic strategies in hormone receptor-positive HER2-negative breast cancer", Cancer Treatment Reviews, vol. 93, (Dec. 7, 2020).
Mullins, et al: "Biomarkers associated with resistance or response to CDK4/6 treatment in patients with metastatic hormone-receptive positive breast cancer", SABCS (Nov. 30, 2018).
Musi, et al; "Pre-clinical evaluation of CDK4/6 inhibitor resistance and immunologic modification in liposarcoma", AACR Annual Meeting (Jun. 1, 2020).
Turner, et al; "Cyclin EI Expression and Palbociclib Efficacy in Previously Treated Hormone Receptor-Positive Metastatic Breast Cancer", J Clin Oncol, vol. 37, No. 14, pp. 1169-1178 (Feb. 26, 2019).
Vijayaraghavan, et al., "CDK4/6 and autophagy inhibitors synergistically induce senescence in Rb positive cytoplasmic cyclin E negative cancers," Nature Communications, vol. 8, No. 1 (Aug. 1, 2017).
Denkert et al. "Penelope HTG" ASCO Jun. 4-8, 2021 Abstract.
Denkert et al. "Subgroup of post-neoadjuvant luminal-B tumors assessed by HTG in Penolope-B investigating palociblib in high risk HER2-/-HR+ breast cancer with residual disease" ASCO Jun. 4-8, 2021 Poster.
Hanley & McNeil Radiology 143: 29-36 (1982).
Loibl et al. "Phase III study of palbociclib combined with endocrine therapy in patients with hormone-receptor-positive, HER2-negative primary breast cancer and high relapse risk after neoadjuvant chemotherapy: First results from Penelope-B" San Antonio Breast Cancer Symposium Dec. 8-11, 2020 Abstract.
Loibl et al. "Phase III study of palbociclib combined with endocrine therapy in patients with hormone-receptor-positive, HER2-negative primary breast cancer and high relapse risk after neoadjuvant chemotherapy: First results from Penelope-B" San Antonio Breast Cancer Symposium Dec. 8-11, 2020 Presentation.
Seeler & Dejean "Sumo and the robustness of cancer" Nature 17: 184-197 (2017).
Sun et al. "Role of ABC Transporters in cancer chemotherapy" Chinese Journal of Cancer 31(2): 51-57 (2012).
Turner et al. "Cyclin E1 Expression and Palbociclib Efficacy in Previously Treated Hormone Receptor-Positive Metastatic Breast Cancer" J Clin Oncol 37: 1-11 (2019).

* cited by examiner

METHOD FOR PREDICTING THE RESPONSE TO CDK4/6 INHIBITOR THERAPY IN CANCER PATIENTS

CROSS-REFERENCE TO RELATED APPLICATIONS

This application is a National Stage entry of International Application No. PCT/EP2022/050876, filed 17 Jan. 2022, which claims priority to European Patent Application No. 21152186.9, filed 18 Jan. 2021, the entire contents of each of which are incorporated herein by reference.

BACKGROUND

Field of the Invention

The present invention is in the field of companion diagnostics and personalized medicine. It relates to methods, kits, systems and uses thereof for prediction of the response or resistance to and/or benefit from a CDK4/6 inhibitor therapy of a subject suffering from a neoplastic disease, in particular breast cancer, based on the measurement(s) of expression level(s) of at least one marker in samples of said subject. Equally, the present invention relates to methods, kits, systems and uses thereof for predicting the outcome from the CDK4/6 inhibitor treatment in said subject based on the measurement(s) of the expression level(s) of the at least one marker in samples of said subject.

Description of Related Art

Cyclin-dependent kinases (CDKs) are the families of serine/threonine protein kinases first discovered for their role in regulating the cell cycle. Cyclin-dependent kinases 4 and 6 (CDK4 and CDK6), which are activated by D-type cyclins, promote cell-cycle entry by phosphorylating Rb (retinoblastoma protein), among other proteins, to initiate transition from the G1 phase to the S phase. They play a key role in regulating cell cycle progression by interacting with specific cyclin proteins in certain tumors. CDKs are therefore a potential target for anti-cancer medication. CDK (cyclin-dependent kinase) inhibitors (CKIs) are any chemicals that inhibit the function of CDKs. They are used to treat cancers by preventing over proliferation of cancer cells. Several CKIs are either approved or in clinical trials. For example, palbociclib (Ibrance®), a CDK4/6 inhibitor, has been approved for use in postmenopausal women with breast cancer that is estrogen receptor positive and human epidermal growth factor receptor 2 (HER2)-negative. Ribociclib (Kisqali®), also an inhibitor of CDK4 and CDK6, has been approved in combination with letrozole for treatment of breast cancer in patients with a hormone receptor positive, HER2-negative advanced metastatic breast cancer. Abemaciclib (Verzenio®) also acts as a selective inhibitor for CDK4 and CDK6. It has been approved for the use for adult patients who have hormone receptor (HR)-positive, HER2-negative advanced or metastatic breast cancer that has progressed after taking therapy that alters a patient's hormones.

Breast cancer cells have receptors on their surface and in their cytoplasm and nucleus. They can be classified according to whether they have three important receptors: estrogen receptor (ER), progesterone receptor (PR), and HER2. ER and PR are hormone receptors (HR). ER+ cancer cells (that is, cancer cells that have estrogen receptors) depend on estrogen for their growth, so they can be treated with drugs to block estrogen effects (e.g. tamoxifen), and generally have a better prognosis. Untreated, HER2+ breast cancers are generally more aggressive than HER2− breast cancers, but HER2+ cancer cells respond to drugs such as the monoclonal antibody trastuzumab (in combination with conventional chemotherapy), and this has improved the prognosis significantly. Cells that do not have any of these three receptor types (estrogen receptors, progesterone receptors, or HER2) are called triple-negative, although they frequently do express receptors for other hormones, such as androgen receptor and prolactin receptor.

About one third of patients with hormone-receptor (HR)-positive, HER2− normal breast cancer and residual disease after neoadjuvant chemotherapy have a substantial risk of relapse. They may thus receive CDK4/6 inhibitor therapy. However, disruption of the CDK-mediated pathways has potentially serious consequences. CDK4/6 inhibitors may have severe side effects including nausea, diarrhea, fatigue, neutropenia, leukopenia, anemia, and thrombocytopenia. Hence, there is a need to identify patients that would benefit from CDK4/6 inhibitor therapy.

SUMMARY

The present invention relates to a method for predicting a response or resistance to and/or a benefit from treatment with an inhibitor of cyclin-dependent kinases 4 (CDK4/6 inhibitor) in a subject suffering from a neoplastic disease such as breast cancer, head and neck cancer, small cell lung cancer (SCLC), non-small cell lung cancer (NSCLC), recurring brain metastasis, squamous cell carcinoma and central nervous system tumor, comprising the step of:

determining in a sample obtained from said subject the expression level of at least one marker selected from the group consisting of Programmed death-ligand 1 (PD-L1), Desmoglein 3 (DSG3), Intraflagellar Transport Protein 52 (IFT52), a marker associated with multidrug resistance such as ATP-binding Cassette Sub-Family B Member 6, mitochondrial (ABCB6), Multidrug resistance-associated protein 1 (ABCC1), ATP-binding Cassette Sub-family A Member 5 (ABCA5), ATP-binding Cassette Sub-family C Member 6 (ABCC6), ATP-binding Cassette transporter Sub-family C Member 11 (ABCC11) and ATP Binding Cassette Subfamily C Member 12 (ABCC12), and a marker associated with SUMOylation such as Protein Inhibitor of Activated STAT 2 (PIAS2), Dual specificity mitogen-activated protein kinase kinase 6 (MAP2K6), Conserved Helix-Loop-Helix Ubiquitous Kinase (CHUK), Small ubiquitin-related modifier 1 (SUM01), G/T mismatch-specific thymine DNA glycosylase (TDG), Aurora Kinase A (AURKA), Structural maintenance of chromosomes protein 3 (SMC3), Inhibitor of Nuclear Factor Kappa-B Kinase Subunit gamma (IKBKG) and Xeroderma pigmentosum, complementation group C (XPC), wherein the expression level of the at least one marker is indicative for predicting the response or resistance to and/or the benefit from the treatment with the CDK4/6 inhibitor in said subject. PD-L1 is encoded by the CD274 gene.

In a particular aspect, the present invention relates to to a method for predicting a response or resistance to and/or a benefit from treatment with an CDK4/6 inhibitor such as palbociclib) (Ibrance®), ribociclib (Kisqal®), abemaciclib (Verzenios®) and trilaciclib, preferably palbociclib, in a subject suffering from breast cancer, comprising the step of:

determining in a sample obtained from said subject the expression level of at least one marker selected from the group consisting of PD-L1, PIAS2, MAP2K6, DSG3, ABCC12 and IFT52, wherein the expression level of the at least one marker is indicative for predicting the response or resistance to and/or the benefit from the treatment with the CDK4/6 inhibitor in said subject.

Typically, with the method of the invention an endpoint such as invasive disease free survival (iDFS) will be predicted.

The marker gene expression may be determined at mRNA and/or protein level, e.g. using gene arrays, sequencing, PCR or immunohistochemistry.

The invention also relates to an CDK4/6 inhibitor for use in the treatment of neoplastic disease in a subject, wherein the subject has been determined to have an increased expression level of at least one marker selected from the group consisting of PD-L1, PIAS2, MAP2K6, DSG3, ABCC12, IFT52, ABCB6, ABCC1, ABCA5, ABCC6, ABCC11, CHUK, SUMO1, TDG, AURKA, SMC3, IKBKG and XPC, preferably consisting of PD-L1, PIAS2, MAP2K6, DSG3, ABCC12 and IFT52, more preferably at least PD-L1, in a sample of said subject.

DETAILED DESCRIPTION OF THE INVENTION

Figure 1:
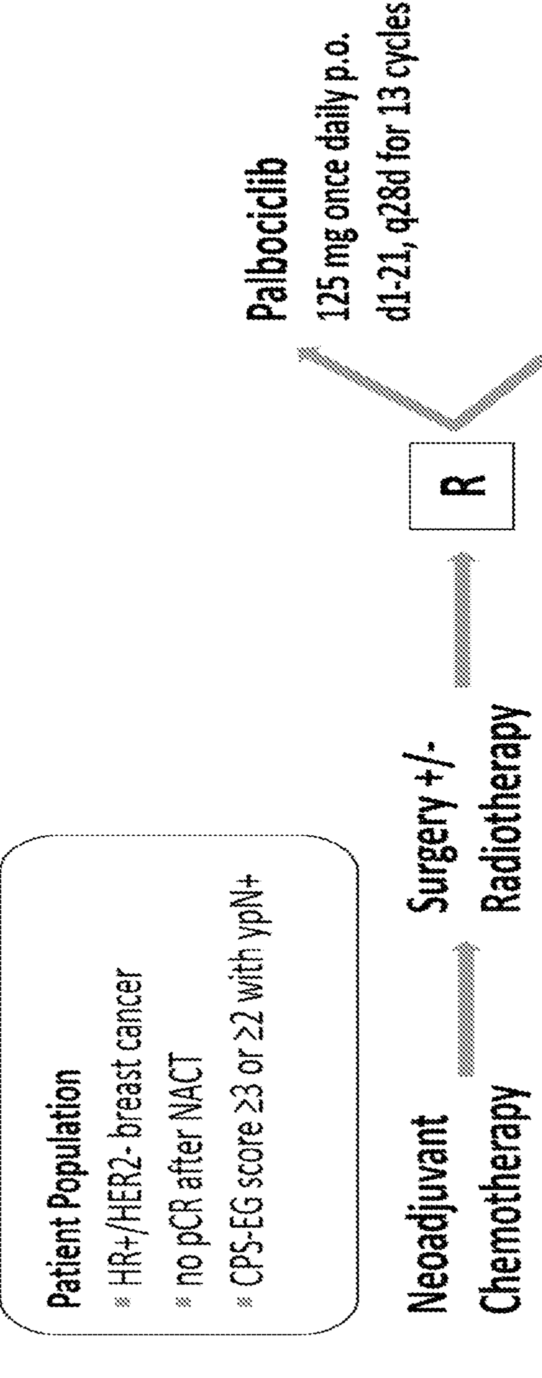
FIG. 1 illustrates the study design of the Penelope$^{B}$ study. R=Randomization (1:1).

Unless defined otherwise, technical and scientific terms used herein have the same meaning as commonly understood by one of ordinary skill in the art to which this invention belongs.

The present invention is based on the inventors' surprising finding that the expression of certain biomarker genes is indicative for a response to or resistance to the treatment with a cyclin-dependent kinases 4 (CDK4/6 inhibitor) in a patient suffering from a neoplastic disease such as breast cancer. Hence, the present invention can be used in predicting a benefit from treatment with CDK4/6 inhibitor and thus allows avoiding such treatment in patients which are not predicted to benefit from the treatment.

In particular, the following biomarkers have been found to be predictive for a benefit from CDK4/6 inhibitor therapy; see Table 2 in the Examples section:

- Programmed death-ligand 1 (PD-L1) (CD274),
- Protein Inhibitor of Activated STAT 2 (PIAS2),
- Dual specificity mitogen-activated protein kinase kinase 6 (MAP2K6),
- Desmoglein 3 (DSG3),
- ATP Binding Cassette Subfamily C Member 12 (ABCC12),
- Intraflagellar Transport Protein 52 (IFT52),
- ATP-binding Cassette Sub-Family B Member 6, mitochondrial (ABCB6),
- Multidrug resistance-associated protein 1 (ABCC1),
- ATP-binding Cassette Sub-family A Member 5 (ABCA5),
- ATP-binding Cassette Sub-family C Member 6 (ABCC6),
- ATP-binding Cassette transporter Sub-family C Member 11 (ABCC11),
- Conserved Helix-Loop-Helix Ubiquitous Kinase (CHUK),
- Small ubiquitin-related modifier 1 (SUMO1),
- G/T mismatch-specific thymine DNA glycosylase (TDG),
- Aurora Kinase A (AURKA),
- Structural maintenance of chromosomes protein 3 (SMC3), and
- Inhibitor of Nuclear Factor Kappa-B Kinase Subunit gamma (IKBKG).

Overexpression of the "Xeroderma pigmentosum, complementation group C" (XPC) gene was found to be linked with a worse outcome in the CDK4/6 inhibitor treatment group compared to patients receiving placebo; see Table 2 in the Examples section. Hence, it is a marker that signals that CDK4/6 inhibitor therapy is contraindicated in the patients.

In particular, the present invention relates in one aspect to a method for predicting a response or resistance to and/or a benefit from treatment with an inhibitor of cyclin-dependent kinases 4 (CDK4/6 inhibitor) in a subject suffering from a neoplastic disease, comprising the step of:

determining in a sample obtained from said subject the expression level of at least one marker selected from the group consisting of Programmed death-ligand 1 (PD-L1), Desmoglein 3 (DSG3), Intraflagellar Transport Protein 52 (IFT52), genes associated with multidrug resistance, and genes associated with SUMOylation, wherein the expression level of the at least one marker is indicative for predicting the response or resistance to and/or the benefit from the treatment with the CDK4/6 inhibitor in said subject.

Hence, the method of the invention can be used for predicting a response to a treatment with a CDK4/6 inhibitor. It can also be used for predicting a resistance to a treatment with a CDK4/6 inhibitor. It can further be used for predicting a benefit from the treatment with CDK4/6 inhibitor. The treatment is for a neoplastic disease as defined herein, particularly breast cancer.

In a particular aspect, (i) the genes associated with multidrug resistance are selected from the group consisting of ATP-binding Cassette Sub-Family B Member 6, mitochondrial (ABCB6), Multidrug resistance-associated protein 1 (ABCC1), ATP-binding Cassette Sub-family A Member 5 (ABCA5), ATP-binding Cassette Sub-family C Member 6 (ABCC6), ATP-binding Cassette transporter Sub-family C Member 11 (ABCC11), and ATP Binding Cassette Subfamily C Member 12 (ABCC12), and/or (ii) the genes associated with SUMOylation are selected form the group consisting of Protein Inhibitor of Activated STAT 2 (PIAS2), Dual specificity mitogen-activated protein kinase kinase 6 (MAP2K6), Conserved Helix-Loop-Helix Ubiquitous Kinase (CHUK), Small ubiquitin-related modifier 1 (SUMO1), G/T mismatch-specific thymine DNA glycosylase (TDG), Aurora Kinase A (AURKA), Structural maintenance of chromosomes protein 3 (SMC3), Inhibitor of Nuclear Factor Kappa-B Kinase Subunit gamma (IKBKG) and Xeroderma pigmentosum, complementation group C (XPC).

In a particular aspect, the marker is selected from the group consisting of PD-L1, PIAS2, MAP2K6, DSG3, ABCC12 and IFT52. In another aspect, the marker is selected from the group consisting of PIAS2, MAP2K6, DSG3, ABCC12 and IFT52. In another aspect, the marker is selected from the group consisting of PIAS2, MAP2K6, DSG3 and ABCC12. In another aspect, the marker is selected from the group consisting of MAP2K6, DSG3, ABCC12 and IFT52. In another aspect, the marker is selected from the group consisting of PIAS2, MAP2K6, ABCC12 and IFT52. In another aspect, the marker is selected from the group consisting of PIAS2, MAP2K6, DSG3 and IFT52. In yet another aspect, the marker is PD-L1. In one aspect, the cancer is luminal breast cancer, the marker is PD-L1 and the endpoint is iDFS.

In particular, the present invention relates in one aspect to a method for predicting a response or resistance to and/or a benefit from treatment with an inhibitor of cyclin-dependent kinases 4 (CDK4/6 inhibitor) in a subject suffering from a neoplastic disease, comprising the step of:

determining in a sample obtained from said subject the expression level of at least one marker selected from the group consisting of Programmed death-ligand 1 (PD-L1), Protein Inhibitor of Activated STAT 2 (PIAS2), Dual specificity mitogen-activated protein kinase kinase 6 (MAP2K6), Desmoglein 3 (DSG3), ATP Binding Cassette Subfamily C Member 12 (ABCC12), Intraflagellar Transport Protein 52 (IFT52), ATP-binding Cassette Sub-Family B Member 6, mitochondrial (ABCB6), Multidrug resistance-associated protein 1 (ABCC1), ATP-binding Cassette Sub-family A Member 5 (ABCA5), ATP-binding Cassette Sub-family C Member 6 (ABCC6), ATP-binding Cassette transporter Subfamily C Member 11 (ABCC11), Conserved Helix-Loop-Helix Ubiquitous Kinase (CHUK), Small ubiquitin-related modifier 1 (SUM01), G/T mismatch-specific thymine DNA glycosylase (TDG), Aurora Kinase A (AURKA), Structural maintenance of chromosomes protein 3 (SMC3), Inhibitor of Nuclear Factor Kappa-B Kinase Subunit gamma (IKBKG) and Xeroderma pigmentosum, complementation group C (XPC), wherein the expression level of the at least one marker is indicative for predicting the response or resistance to and/or the benefit from the treatment with the CDK4/6 inhibitor in said subject.

Notably, several of these genes are associated with multidrug resistance (MDR), particularly ATP-binding cassette (ABC) transporter genes ABCC12, ABCB6, ABCC1, ABCA5, ABCC6, ABCC11. MDR in cancer cells can significantly attenuate the response to chemotherapy and increase the likelihood of mortality. The major mechanism involved in conferring MDR is the overexpression of ATP-binding cassette (ABC) transporters, which can increase efflux of drugs from cancer cells, thereby decreasing intracellular drug concentration (Sun et al., Chin J Cancer 31(2): 51-57 (2012)).

Several other markers herein belong to the pathway associated with proteins of the small ubiquitin-related modifier (SUMO) family: PIAS2, MAP2K6, CHUK, SUMO1, TDG, AURKA, SMC3, IKBKG and XPC. Post-translational protein modification by small ubiquitin-like modifier (SUMO), termed sumoylation (or SUMOylation), has been implicated as an important mechanism in cellular responses to stress and one that appears to be upregulated in many cancers (Seeler & Dejean, Nature Reviews Cancer volume 17, pages 184-197 (2017)).

Hence, in particular aspects of the present invention the at least one marker determined is selected from these ABC transporter genes and/or the genes associated with the SUMO pathway. The term "marker associated with SUMOylation" herein refers to markers that are associated with the SUMO pathway.

In a particular aspect of the method of the invention the at least one marker is selected from the group consisting of PD-L1, PIAS2, MAP2K6, DSG3, ABCC12 and IFT52. These markers show particular high correlations with the outcome of CDK4/6 inhibitor therapy; see Table 2 in the Examples section.

In yet another particular aspect, the marker is PD-L1.

As indicated, several markers can be combined in a marker panel in order to refine results of the prognosis. Hence, the expression level of at least two, three, four or five or even more markers selected from the markers mentioned herein above and in particular from the group consisting of PD-L1, PIAS2, MAP2K6, DSG3, ABCC12 and IFT52 can be determined in said sample. They can, however, in addition also be combined with further biomarkers and/or other clinical or non-clinical parameters of the respective patient. Clinical parameters may for example be selected the group consisting of pathological grading of the tumor, tumor size, nodal status, proliferation (in particular Ki-67), and immune system markers (in particular lymphocytes). Non-clinical parameters e.g. comprise age, sex, body weight and/or body-mass index (BMI).

The method of the invention may further comprise the determination of the expression level of Cyclin E1 (CCNE1; also known as G1/S-specific cyclin-E1). High CCNE1 mRNA expression has been shown to be associated with relative resistance to palbociclib (Turner et al.; J Clin Oncol. 37(14):1169-1178 (2019))

An exemplary marker panel may comprise or consist of PIAS2, MAP2K6, DSG3, ABCC12 and IFT52. Another exemplary marker panel may comprise or consist of PD-L1, PIAS2, MAP2K6, DSG3, ABCC12 and IFT52. For instance, the expression levels of a set of genes may be determined in the patient's sample and mathematically combined into a score, e.g. wherein said set of genes contains two or more genes of PD-L1, PIAS2, MAP2K6, DSG3, ABCC12 and IFT52.

Another relevant marker panel may comprise or consist of PD-L1, ABCA5, ABCB6, ABCC1, ABCC12, CALML3, CCL13, DSG3, HPSE, IL1RAP, MAP2K6, NF2, PEX12 and PIAS2. This panel corresponds to "Signature 2" in Example 5. Yet another relevant marker panel may comprise or consist of ABCA5, ABCB6, ABCC1, ABCC12, CALML3, CCL13, DSG3, HPSE, IL1RAP, MAP2K6, NF2, PEX12 and PIAS2. This panel corresponds to "Signature 1" in Example 4.

Thus, in one aspect of the method of the present invention a panel of two or more markers is determined, e.g. at least two, three, four, five, six, seven, eight, nine, ten, eleven, twelve or thirteen or all markers selected from the group consisting of PD-L1, ABCA5, ABCB6, ABCC1, ABCC12, CALML3, CCL13, DSG3, HPSE, IL1RAP, MAP2K6, NF2, PEX12 and PIAS2 is determined in said sample. In another aspect of the method of the present invention a panel of two or more markers is determined, e.g. at least two, three, four, five, six, seven, eight, nine, ten, eleven or twelve or all markers selected from the group consisting of ABCA5, ABCB6, ABCC1, ABCC12, CALML3, CCL13, DSG3, HPSE, IL1RAP, MAP2K6, NF2, PEX12 and PIAS2 is determined in said sample.

Particular subset marker panels comprise or consist of the markers "ABCA5, ABCB6, ABCC1, DSG3, MAP2K6, NF2, PIAS2, and CD274" or "ABCC1, DSG3, MAP2K6, NF2, and PIAS2".

In principle, the invention applies to neoplastic diseases in general that can and are treated with CDK4/6 inhibitors. These can be primary and metastazing cancers. Typically, the neoplastic disease is a solid tumor. In a particular aspect, the neoplastic disease is a disease selected from the group consisting of breast cancer, head and neck cancer, small cell lung cancer (SCLC), non-small cell lung cancer (NSCLC), recurring brain metastasis, squamous cell carcinoma and central nervous system tumor. Breast cancer is the most typical disease herein, preferably primary breast cancer. In a very particular aspect of the invention, the breast cancer is hormone receptor (HR)-positive, human epidermal growth factor receptor 2 (HER2)-negative (sometimes referred to as "luminal" or "luminal A" breast cancer) either primary diagnosed or locally advanced or metastatic breast cancer. It can also be metastatic triple negative breast cancer (mTNBC).

Hence, typically the sample in the context of the present invention is a tumor tissue sample such as a primary tumor tissue sample, particularly a core biopsy sample, more particularly a core biopsy sample from a primary tumor before any treatment. It may, however, also be a post-surgical residual tumor tissue sample or a post-surgical lymph node sample. In one typical application, the sample is a formalin-fixed, paraffin-embedded (FFPE) tumor tissue sample.

The CDK4/6 inhibitor in the context of the present invention may e.g. be selected from the group consisting of palbociclib)(Ibrance®), ribociclib)(Kisqal®), abemaciclib (Verzenios®) and trilaciclib. In a particular aspect, the CDK4/6 inhibitor is palbociclib.

Determination of the expression level of the marker genes herein can in principle be determined at mRNA and/or protein level. When determined at mRNA level, the expression level may e.g. be determined in a hybridization-based method, a PCR based method, a microarray-based method, a sequencing and/or next generation sequencing method. When determined at protein level, immunoassay methods are typically used, e.g. an immunohistochemistry (IHC) assay (which is of particular interest for PD-L1).

In the context of the present invention the response, resistance and/or benefit is typically determined in terms of the invasive disease-free survival (iDFS), distant-disease-free survival (DDFS), pathological complete response (pCR), loco-regional recurrence free interval (LRRFI), loco-regional invasive recurrence free interval (LRIRFI), disease free survival (DFS), event free survival (EFS) and/or overall survival (OS). The most typical endpoint in the context of the present invention is iDFS.

Typically, for the markers mentioned herein above in the context of the present invention a higher expression is associated with a higher likelihood of benefit from the CDK4/6 inhibitor, and/or a lower expression is associated with a lower benefit, no benefit or a disadvantage from the CDK4/6 inhibitor. The exception is the XPC gene: a lower XPC expression is associated with a higher likelihood of benefit from the CDK4/6 inhibitor, and/or a higher XPC expression is associated with a lower benefit, no benefit or a disadvantage from the CDK4/6 inhibitor.

Also typically in the context of the present invention, the method comprises comparing the expression level of each of said at least one marker to a predetermined reference level, wherein patients with expression level above the reference level have a high likelihood of benefit from the CDK4/6 inhibitor, and wherein patients with low expression level have no benefit or a disadvantage from the CDK4/6 inhibitor.

The reference level for a particular patient depends on his/her individual prognosis for the disease and individual risk of adverse effects from the CDK4/6 inhibitor.

The present invention also relates to an CDK4/6 inhibitor for use in the treatment of neoplastic disease in a subject, wherein the subject has been determined to have an increased expression level of at least one marker selected from the group consisting of PD-L1, PIAS2, MAP2K6, DSG3, ABCC12, IFT52, ABCB6, ABCC1, ABCA5, ABCC6, ABCC11, CHUK, SUM01, TDG, AURKA, SMC3, IKBKG and XPC, preferably consisting of PD-L1, PIAS2, MAP2K6, DSG3, ABCC12 and IFT52, more preferably at least PD-L1, in a sample of said subject. However, marker panels as discussed herein above may be used in this context.

Similarly, the present invention relates to a method of treating a neoplastic disease in a subject with a CDK4/6 inhibitor, wherein the subject has been determined to have (i) an increased expression level of at least one marker selected from the group consisting of PD-L1, PIAS2, MAP2K6, DSG3, ABCC12, IFT52, ABCB6, ABCC1, ABCA5, ABCC6, ABCC11, CHUK, SUMO1, TDG, AURKA, SMC3, IKBKG (preferably consisting of PD-L1, PIAS2, MAP2K6, DSG3, ABCC12 and IFT52, more preferably comprising at least PD-L1) and/or (i) a decreased expression level of XPC in a sample of said subject.

As mentioned, CDK4/6 inhibitor may e.g. be selected from the group consisting of palbociclib, ribociclib, abemaciclib and trilaciclib, preferably it is palbociclib.

The neoplastic disease to be treated may be a disease as defined herein above, e.g. selected form the group consisting of breast cancer, head and neck cancer, non-small cell lung cancer, recurring brain metastasis, squamous cell carcinoma and central nervous system tumor, preferably breast cancer. In a particular aspect the breast cancer is hormone receptor (HR)-positive, human epidermal growth factor receptor 2 (HER2)-negative breast cancer. The treatment with the CDK4/6 inhibitor may be after neoadjuvant chemotherapy and surgery. It may be combined with an endocrine therapy such as an aromatase inhibitor, tamoxifen, fulvestrant, or a luteinizing hormone-releasing hormone (LHRH) agonist or analogue. In a very particular aspect, the treatment is combined with the administration of fulvestrant and wherein the subject is a female patient suffering from hormone receptor (HR)-positive, human epidermal growth factor receptor 2 (HER2)-negative locally advanced or metastatic breast cancer who has received prior endocrine therapy.

As mentioned, the CDK4/6 inhibitor may be used in combination with fulvestrant, tamoxifen and/or aromatase inhibitors. Fulvestrant is e.g. used to treat certain types of breast cancer. Breast cancer cells need the hormone estrogen in order to grow. Fulvestrant works by blocking the effect of estrogen, slowing tumor cell growth. Tamoxifen (Nolvadex®) is a selective estrogen receptor modulator that is used for the treatment of both early and advanced estrogen receptor-positive breast cancer in pre- and postmenopausal women and in male breast cancer patients. Aromatase inhibitors are medications that treat breast cancer in both early stages and advanced ones. They prevent your body from making estrogen. They only work in women who are past menopause, though.

DETAILED DEFINITIONS

Neoadjuvant chemotherapy refers to medicines that are administered before surgery. Adjuvant (meaning "in addition to") chemotherapy refers to medicines administered after surgery For the purposes of the present invention, the "subject" (or "patient") may be a mammal. In the context of the present invention, the term "subject" includes both humans and other mammals. Thus, the herein provided methods are applicable to both human and animal subjects, i.e. the method can be used for medical and veterinary purposes. Accordingly, said subject may be an animal such as a mouse, rat, hamster, rabbit, guinea pig, ferret, cat, dog, sheep, bovine species, horse, camel, or primate. Most preferably herein the subject is human. However, the diagnosis and treatment of canine, feline and equine mammals is of further particular interest. The subject may in principle be female and male, female may be pre- or perimenopausal. In the context of breast cancer, female subjects are more often diseased than male subjects.

The subject may be treated with further other components, such as chemotherapeutic agents and/or non-chemotherapeutic agents in both groups. A predictive marker relates to a marker which can be used to predict the response or resistance and/or benefit of the subject towards a given treatment, e.g. the treatment with the CDK4/6 inhibitor. As used herein, the term "predicting the response to a treatment with a CDK4/6 inhibitor" refers to the act of determining a likely response or resistance and/or benefit of the CDK4/6 inhibitor therapy in a subject suffering from neoplastic disease. The prediction of a response or resistance and/or benefit is preferably made with reference to a reference value described below in detail. The predictive methods of the present invention can be used clinically to make treatment decisions by choosing the most appropriate treatment modalities for the subject.

As used herein, the terms "predicting an outcome" and "prediction of an outcome" of a disease are used interchangeably and refer to a prediction of an outcome of a patient undergoing a given therapy, i.e. the CDK4/6 inhibitor therapy. The terms "predicting an outcome" and "prediction of an outcome" may, in particular, relate to an individual assessment of the malignancy of a tumor, or to the expected survival rate (OS, overall survival or DFS, disease free survival) of a patient, if the tumor is treated with a given therapy, i.e. the treatment the CDK4/6 inhibitor.

As used herein, the term "predicting a resistance to the CDK4/6 inhibitor therapy" relates to a prediction of a resistance of a patient undergoing a given therapy, i.e. the CDK4/6 inhibitor therapy. The term "predicting a resistance to the CDK4/6 inhibitor therapy" may, in particular, relate to a non-response and/or a non-benefit in said subject by individual assessment of the malignancy of a tumor, or to the expected survival rate (OS, overall survival or DFS, disease free survival) of a patient, if the tumor is treated with a given therapy, i.e. the CDK4/6 inhibitor therapy.

The term "prognosis" or "prognosticate" relates to an individual assessment of the malignancy of a tumor or disease outcome of a patient treated with a given therapy. In opposite to the term "prediction" defined above, the term "prognosis" does not compare different treatments.

As used herein, the term "treatment", "treat", "treating" and grammatical variations thereof refer to subjecting an individual subject to a protocol, regimen, process or remedy, in which it is desired to obtain a physiologic response or outcome in that subject, e.g., a patient. In particular, the methods and compositions of the present invention may be used to slow the development of disease symptoms or delay the onset of the disease or condition, or halt the progression of disease development. However, because every treated subject may not respond to a particular treatment protocol, regimen, process or remedy, treating does not require that the desired physiologic response or outcome be achieved in each and every subject or subject population, e.g., patient population. Accordingly, a given subject or subject population, e.g., patient population may fail to respond or respond inadequately to treatment.

As used herein, the term "disease" is defined as a deviation from the normal structure or function of any part, organ or system of the body (or any combination thereof). A specific disease is manifested by characteristic symptoms and signs, including both chemical and physical changes. Certain characteristic signs, symptoms, and related factors of the disease can be quantitated through a variety of methods to yield important diagnostic information. For example, the neoplastic disease may be a tumor or cancer. As used herein, the term "tumor" refers to all neoplastic cell growth and proliferation, whether malignant or benign, and all pre-cancerous and cancerous cells and tissues. As used herein, the term "cancer" refers to uncontrolled cellular growth, and is not limited to any stage, grade, histomorphological feature, invasiveness, aggressivity, or malignancy of an affected tissue or cell aggregation. For example, stage 0 breast cancer, stage I breast cancer, stage II breast cancer, stage III breast cancer, stage IV breast cancer, grade I breast cancer, grade II breast cancer, grade III breast cancer, malignant breast cancer, primary carcinomas of the breast, and all other types of cancers, malignancies and transformations associated with the breast are included. As used herein, the term "neoplastic lesion" or "neoplastic disease" or "neoplasia" refers to a cancerous tissue this includes carcinomas, (e.g., carcinoma in situ, invasive carcinoma, metastatic carcinoma) and pre-malignant conditions, neomorphic changes independent of their histological origin (e.g. ductal, lobular, medullary, mixed origin).

The neoplastic disease can be an early, non-metastatic neoplastic disease or a recurrent and/or metastatic neoplastic disease. As used herein, the term "recurrent" refers in particular to the occurrence of metastasis. Such metastasis may be distal metastasis that can appear after the initial diagnosis, even after many years, and therapy of a tumor, to local events such as infiltration of tumor cells into regional lymph nodes, or occurrence of tumor cells at the same site and organ of origin. The term "early" as used herein refers to non-metastatic diseases, in particular cancer. In one embodiment, the neoplastic disease is a non-metastatic disease.

As mentioned herein above, in a preferred embodiment, the neoplastic disease may be breast cancer. Along with classification of histological type and grade, breast cancers are routinely evaluated for expression of hormone receptors (estrogen receptor (ER) and progesterone receptor (PR)) and for expression of HER2 (ErbB2). ER and PR are both nuclear receptors (they are predominantly located at cell nuclei, although they can also be found at the cell membrane). HER2, or human epidermal growth factor receptor type 2, is a receptor normally located on the cell surface.

In a more particular embodiment, the neoplastic disease is primary triple negative breast cancer (TNBC). As used herein, the term "triple negative" or "TN" refers to tumors (e.g., carcinomas), typically breast tumors, in which the tumor cells score negative (i.e., using conventional histopathology methods) for estrogen receptor (ER) and progesterone receptor (PR), both of which are nuclear receptors (i.e., they are predominantly located at cell nuclei), and the tumor cells are not amplified for epidermal growth factor receptor type 2 (HER2 or ErbB2), a receptor normally located on the cell surface. Furthermore, the term "triple negative breast cancer(s)" or "TN breast cancer(s)" encompasses carcinomas of differing histopathological phenotypes. For example, certain TN breast cancers are classified as "basal-like" ("BL"), in which the neoplastic cells express genes usually found in normal basal/myoepithelial cells of the breast, such as high molecular weight basal cytokeratins (CK, CK5/6, CK14, CK17), vimentin, p-cadherin, ccB crystallin, fascin and caveolins 1 and 2. Certain other TN breast cancers, however, have a different histopathological phenotype, examples of which include high grade invasive ductal carcinoma of no special type, metaplastic carcinomas, medullary carcinomas and salivary gland-like tumors of the breast.

As used herein, the terms "sample" or "biological sample" as are used interchangeably and refer to a sample obtained from the subject. The sample may be of any biological tissue or fluid suitable for carrying out the method of the present invention, i.e. for assessing whether a subject suffering from a neoplastic disease, in particular breast cancer, will respond or be resistant to and/or benefit from the the CDK4/6 inhibitor therapy and/or for assessing the outcome of said patient to the CDK4/6 inhibitor therapy. However, typically, once the subject's is determined to have a response and/or benefit and/or good outcome with the CDK4/6 inhibitor therapy according to the methods of the present invention, the subject will receive the CDK4/6 inhibitor therapy as soon as possible.

In particular, the sample may be obtained from any tissue and/or fluid of a subject suffering from a neoplastic disease. Preferably, the tissue and/or fluid of the sample may be taken from any material of the neoplastic disease and/or from any material associated with the neoplastic disease. Such a sample may, for example, comprise cells obtained from the subject. In one embodiment, the sample may be a tumor sample. A "tumor sample" is a biological sample containing tumor cells, whether intact or degraded. In one embodiment, the sample is a tumor sample obtained from said subject. The sample may also be a bodily fluid. Such fluids may include the lymph. In one embodiment, the sample is a lymph node sample obtained from said subject. In another embodiment, the sample is a tumor sample or a lymph node sample obtained from said subject.

The sample may also include sections of tissues. Such sections of tissues also encompass frozen or fixed sections. These frozen or fixed sections may be used, e.g. for histological purposes. In one embodiment, the sample from said subject is a formalin-fixed paraffin embedded sample or a fresh-frozen sample.

A sample to be analyzed may be taken by aspiration or punctuation, excision or by any other surgical method leading to biopsy or resected cellular material.

As used herein, the term "expression level of the at least one marker" refers to the quantity of the molecular entity of the marker in a sample that is obtained from the subject. In other words, the concentration of the marker is determined in the sample. It is also envisaged that a fragment of the marker can be detected and quantified. Thus, it is apparent to the person skilled in the art, in order to determine the expression of a marker, parts and fragments of said marker can be used instead. Suitable method to determine the expression level of the at least one marker are described herein below in detail. As used herein, the term "marker" relates to measurable and quantifiable biological markers which serve as indices for health- and physiology-related assessments, such as a disease/disorder/clinical condition risk. Furthermore, a marker is defined as a characteristic that is objectively measured and evaluated as an indicator of normal biological processes, pathogenic processes, or pharmacologic responses to a therapeutic intervention. As discussed herein above a biomarker may be measured on a biological sample (e.g., as a tissue test).

In one embodiment, the expression level of the at least one marker is the protein expression level or the RNA expression level, preferably mRNA expression level. For example, the expression level refers to a determined level of gene expression. A "gene" is a set of segments of nucleic acid that contains the information necessary to produce a functional RNA product. A "gene product" is a biological molecule produced through transcription or expression of a gene, e.g., an mRNA, cDNA or the translated protein. An "mRNA" is the transcribed product of a gene and shall have the ordinary meaning understood by a person skilled in the art. A "molecule derived from an mRNA" is a molecule which is chemically or enzymatically obtained from an mRNA template, such as cDNA. The expression level may be a determined level of protein, RNA, or mRNA expression as an absolute value or compared to a reference gene, to the average of two or more reference value, or to a computed average expression value or to another informative protein, RNA or mRNA without the use of a reference sample.

The gene names as used in the context of the present invention refer to gene names according to the official gene symbols provided by the HGNC (HUGO Gene Nomenclature Committee) and as used by the NCBI (National Center for Biotechnology Information).

When referring to markers of the present invention as identified by the gene names mentioned herein above, the person skilled in the art how to derive the respective RNA, in particular the mRNA, or the protein of the marker identified by its gene name.

In one embodiment, the expression level is the RNA expression level, preferably mRNA expression level, and is determined by at least one of a hybridization based method, a PCR based method, a microarray based method, a sequencing and/or next generation sequencing approach. The term "a PCR based method" as used herein refers to methods comprising a polymerase chain reaction (PCR). This is a method of exponentially amplifying nucleic acids, e.g. DNA by enzymatic replication in vitro. As PCR is an in vitro technique, it can be performed without restrictions on the form of DNA, and it can be extensively modified to perform a wide array of genetic manipulations. When it comes to the determination of expression levels, a PCR based method may for example be used to detect the presence of a given mRNA by (1) reverse transcription of the complete mRNA pool (the so called transcriptome) into cDNA with help of a reverse transcriptase enzyme, and (2) detecting the presence of a given cDNA with help of respective primers. This approach is commonly known as reverse transcriptase PCR (rtPCR). Moreover, PCR-based methods comprise e.g. real time PCR, and, particularly suited for the analysis of expression levels, kinetic or quantitative PCR (qPCR).

The term "Quantitative PCR" (qPCR)" refers to any type of a PCR method which allows the quantification of the template in a sample. Quantitative real-time PCR comprise different techniques of performance or product detection as for example the TaqMan technique or the LightCycler technique. The TaqMan technique, for examples, uses a dual-labelled fluorogenic probe. The TaqMan real-time PCR measures accumulation of a product via the fluorophore during the exponential stages of the PCR, rather than at the end point as in conventional PCR. The exponential increase of the product is used to determine the threshold cycle, CT, e.g., the number of PCR cycles at which a significant exponential increase in fluorescence is detected, and which is directly correlated with the number of copies of DNA template present in the reaction. The set-up of the reaction is very similar to a conventional PCR, but is carried out in a real-time thermal cycler that allows measurement of fluorescent molecules in the PCR tubes. Different from regular PCR, in TaqMan real-time PCR a probe is added to the reaction, e.g., a single-stranded oligonucleotide complementary to a segment of 20-60 nucleotides within the DNA template and located between the two primers. A fluorescent reporter or fluorophore (e.g., 6-carboxyfluorescein, acronym: FAM, or tetrachlorofluorescin, acronym: TET) and quencher (e.g., tetramethylrhodamine, acronym: TAMRA, of dihydrocyclopyrroloindole tripeptide 'black hole quencher', acronym: BHQ) are covalently attached to the 5' and 3' ends of the probe, respectively. The close proximity between fluorophore and quencher attached to the probe inhibits fluorescence from the fluorophore. During PCR, as DNA synthesis commences, the 5' to 3' exonuclease activity of the Taq polymerase degrades that proportion of the probe that has annealed to the template. Degradation of the probe releases the fluorophore from it and breaks the close proximity to the quencher, thus relieving the quenching effect and allowing fluorescence of the fluorophore. Hence, fluorescence detected in the real time PCR thermal cycler is directly proportional to the fluorophore released and the amount of DNA template present in the PCR.

As used herein, the term "hybridization based method" refers to a method, wherein complementary, single-stranded nucleic acids or nucleotide analogues may be combined into a single double stranded molecule. Nucleotides or nucleotide analogues will bind to their complement under normal conditions, so two complementary strands will bind to each other. In bioanalytics, very often labelled, single stranded probes are in order to find complementary target sequences. If such sequences exist in the sample, the probes will hybridize to said sequences which can then be detected due to the label. Other hybridization based methods comprise microarray and/or biochip methods. For example, probes may be immobilized on a solid phase, which is then exposed to a sample. If complementary nucleic acids exist in the sample, these will hybridize to the probes and can thus be detected. These approaches are also known as "array based methods". Yet another hybridization based method is PCR, which is described above. When it comes to the determination of expression levels, hybridization based methods may for example be used to determine the amount of mRNA for a given gene. An oligonucleotide capable of specifically binding sequences a gene or fragments thereof relates to an oligonucleotide which specifically hybridizes to a gene or gene product, such as the gene's mRNA or cDNA or to a fragment thereof. To specifically detect the gene or gene product, it is not necessary to detect the entire gene sequence. A fragment of about 20-150 bases will contain enough sequence specific information to allow specific hybridization.

By "array" or "matrix" an arrangement of addressable locations or "addresses" on a device is meant. The locations can be arranged in two dimensional arrays, three dimensional arrays, or other matrix formats. The number of locations can range from several to at least hundreds of thousands. Most importantly, each location represents a totally independent reaction site. Arrays include but are not limited to nucleic acid arrays, protein arrays and antibody arrays. A "nucleic acid array" refers to an array containing nucleic acid probes, such as oligonucleotides, nucleotide analogues, polynucleotides, polymers of nucleotide analogues, morpholino oligomers or larger portions of genes. The nucleic acid and/or analogue on the array is preferably single stranded. Arrays wherein the probes are oligonucleotides are referred to as "oligonucleotide arrays" or "oligonucleotide chips." A "microarray," herein also refers to a "biochip" or "biological chip", an array of regions having a density of discrete regions of at least about $100/cm^2$, and preferably at least about $1000/cm^2$.

In one embodiment, the expression level of the at least one marker may be the protein level. It is clear to the person skilled in the art that a reference to a nucleotide sequence may comprise reference to the associated protein sequence which is coded by said nucleotide sequence. The expression level of a protein may be measured indirectly, e.g. by obtaining a signal wherein the signal strength is correlated to the amount of mRNA transcripts of that gene or it may be obtained directly at a protein level, e.g., by immunohistochemistry, CISH, ELISA (enzyme linked immunoassay), RIA (radioimmunoassay) or the use of protein microarrays, two-hybrid screening, blotting methods including western blot, one- and two dimensional gel electrophoresis, isoelectric focusing as well as methods being based on mass spectrometry like MALDI-TOF and the like. The term "immunohistochemistry" or IHC refers to the process of localizing proteins in cells of a tissue section exploiting the principle of antibodies binding specifically to antigens in biological tissues. Immunohistochemical staining is widely used in the diagnosis and treatment of cancer. Specific molecular markers are characteristic of particular cancer types. IHC is also widely used in basic research to understand the distribution and localization of biomarkers in different parts of a tissue.

Quantitative methods such as targeted RNA sequencing, modified nuclease protection assays, hybridization-based assays and quantitative PCR are particularly preferred herein.

As used herein, the term "response" refers to any response to the CDK4/6 inhibitor therapy. Non-limiting examples commonly used in oncology to evaluate the response of the subject to a therapy may be a change in tumor mass and/or volume and/or prolongation of time to distant metastasis or time to death following treatment. As used herein, "benefit" from a given therapy is an improvement in health or well-being that can be observed in patients under said therapy, but it is not observed in patients not receiving this therapy. Non-limiting examples commonly used in oncology to gauge a benefit from therapy are survival, disease free survival, metastasis free survival, disappearance of metastasis, tumor regression, and tumor remission. Vice versa, the term "resistance" as used herein refers to any non-response and or non-benefit to the CDK4/6 inhibitor therapy. Non-limiting examples commonly used in oncology to evaluate the resistance of the subject to a therapy may be a change in tumor mass and/or volume and/or shorter time to distant metastasis or time to death following treatment.

The benefit and/or response or resistance may be assessed in a neoadjuvant situation where the size of a tumor after systemic intervention can be compared to the initial size and dimensions as measured by CT, PET, mammogram, ultrasound or palpation, usually recorded as "clinical response" of a patient. Response or resistance and/or benefit may also be assessed by caliper measurement or pathological examination of the tumor after biopsy or surgical resection. Response or resistance and/or benefit may be recorded in a quantitative fashion like percentage change in tumor volume or in a qualitative fashion like "no change" (NC), "partial remission" (PR), "complete remission" (CR) or other qualitative criteria. Assessment of tumor response or resistance and/or benefit may be done early after the onset of neoadjuvant therapy e.g. after a few hours, days, weeks or preferably after a few months. A typical endpoint for response or resistance and/or benefit assessment is upon termination of neoadjuvant chemotherapy or upon surgical removal of residual tumor cells and/or the tumor bed. Response or resistance and/or benefit may also be assessed by comparing time to distant metastasis or death of a patient following neoadjuvant or adjuvant non-chemotherapy and/or chemotherapy with time to distant metastasis or death of a patient not treated with non-chemotherapy and/or chemotherapy.

In one embodiment, the response or resistance and/or benefit of the subject is the disease free survival (DFS). In a preferred embodiment, the DFS may be selected from the list consisting of the pathological complete response (pCR); clinical response; loco-regional recurrence free interval (LRRFI); loco-regional invasive recurrence free interval (LRIRFI); distant-disease-free survival (DDFS); invasive disease-free survival (iDFS); event free survival (EFS) and/or overall survival (OS).

As used herein, the terms "pCR" and "pathological complete response" are used interchangeably and are well understood by the person skilled in the art.

As used herein, the term "clinical response" is well understood by the person skilled in the art and may include clinical response with levels of complete response, partial response, stable disease, progressive disease.

As used herein, the term "outcome" refers to a condition attained in the course of a disease. This disease outcome may e.g. be a clinical condition such as "recurrence of disease", "development of metastasis", "development of nodal metastasis", "development of distant metastasis", "survival", "death", "tumor remission rate", a disease stage or grade or the like. In one embodiment, the outcome is the pathological complete response (pCR), loco-regional recurrence free interval (LRRFI), loco-regional invasive recurrence free interval (LRIRFI), distant-disease-free survival (DDFS), invasive disease-free survival (iDFS), event free survival (EFS) and/or overall survival (OS).

In one embodiment, the response and/or benefit and/or outcome may be the pCR. As used herein, the term "pathological complete response" (pCR) refers to a complete disappearance or absence of invasive tumor cells in the breast and/or lymph nodes as assessed by a histopathological examination.

Typically, said expression level of the at least one marker or a mathematical combination of expression levels of two or more markers ("score") is compared to a reference level. Such "reference-value" can be a numerical cutoff value, it can be derived from a reference measurement of one or more other marker in the same sample, or one or more other marker and/or the same marker in one other sample or in a plurality of other samples. In one embodiment, the method comprises comparing the expression level of each of said at least one marker to a predetermined reference level. In another embodiment the reference value can be determined from a validation cohort, preferentially as the median or any other percentile, or preferentially by specifying one or more aims for statistical measures such as specificity, sensitivity, negative predictive value, positive predictive value, overall correctness, area under receiver operator curve, odds ratio, hazard ratio, or c-index.

The response or resistance to and/or the benefit from a CDK4/6 inhibitor therapy in a subject suffering from a neoplastic disease, in particular breast cancer, may be predicted based on the comparison of the expression level of the at least one marker with the reference level. In another embodiment, the outcome of the CDK4/6 inhibitor therapy in a subject suffering from a neoplastic disease, in particular breast cancer, may be prognosticated based on the comparison of the expression level of the at least one marker with the reference level. In another embodiment, the response or resistance to and/or the benefit from the CDK4/6 inhibitor therapy in a subject suffering from a neoplastic disease, in particular breast cancer, may be predicted and the outcome of the CDK4/6 inhibitor therapy in a subject suffering from a neoplastic disease, in particular breast cancer, may be prognosticated based on the comparison of the expression level of the at least one marker with the reference level. Such a reference level can e.g. be predetermined level that has been determined based on a population of healthy subjects. In one embodiment, the reference level comprises the expression level of the at least one marker in a sample obtained from at least one healthy subject, preferably the mean expression level of the at least one marker in samples obtained from a healthy population.

The reference value may be lower or higher than the expression level of the at least one marker. For example, the reference value may be 2-fold lower or 2-fold higher than the expression level of the at least one marker. The difference between the expression level of the at least one marker compared to the reference value may alternatively be determined by absolute values, e.g. by the difference of the expression level of the at least one marker and the reference value, or by relative values, e.g. by the percentage increase or decrease of the expression level of the at least one marker compared to the reference value. The expression level of the at least one marker which deviates from the reference value may be indicative for a particular response and/or benefit and/or outcome of the CDK4/6 inhibitor therapy in a subject suffering from a neoplastic disease, in particular breast cancer. In other words, an upregulation or a downregulation of the expression level of the at least one marker compared to the reference value may be indicative for a response and/or benefit and/or good outcome from a treatment with the CDK4/6 inhibitor therapy in said subject. In particular, the extent of upregulation of the expression level of the at least one marker compared to the reference value may be indicative for a particular response and/or benefit and/or outcome of the CDK4/6 inhibitor therapy in a subject suffering from a neoplastic disease, in particular breast cancer. For example, the expression level of the at least one marker above by 3-fold rather than above 2-fold compared to the reference value may be indicative with a higher likelihood for a response and/or benefit from the CDK4/6 inhibitor therapy in said subject.

In one embodiment, the comparison of the expression level of the at least one marker to the reference value indicates the likelihood of the subject for a response and/or benefit of a treatment with the CDK4/6 inhibitor therapy. In another embodiment, the comparison of the expression level of the at least one marker to the reference value indicates the likelihood of the subject for an outcome of a treatment with the CDK4/6 inhibitor therapy. In another embodiment, the comparison of the expression level of the at least one marker to the reference value indicates the likelihood of the subject for a response and/or benefit of a treatment with the CDK4/6 inhibitor therapy and/or the likelihood of the subject for an outcome of a treatment with the CDK4/6 inhibitor therapy.

In one embodiment, an expression level of the at least one marker above said reference level in the sample is indicative for a response and/or benefit from a treatment with a CDK4/6 inhibitor therapy in said subject. In another embodiment, an expression level of the at least one marker above said reference level in the sample is indicative for an improved outcome of a treatment with a CDK4/6 inhibitor therapy in said subject compared to a therapy without a CDK4/6 inhibitor.

The skilled artisan will understand that associating a diagnostic or prognostic indicator, i.e. the expression level of the at least one marker, with the prediction of a response, benefit or with a prognostic risk of a future clinical outcome is a statistical analysis. For example, a marker level of lower than X may signal that a subject is more likely to suffer from an adverse outcome than a subject with a level more than or equal to X, as determined by a level of statistical significance. Additionally, a change in marker concentration from baseline levels may be reflective of subject prognosis, and the degree of change in marker level may be related to the severity of adverse events. Statistical significance is often determined by comparing two or more populations, and determining a confidence interval and/or a p value; see, e.g., Dowdy and Wearden, Statistics for Research, John Wiley & Sons, New York, 1983. Preferred confidence intervals of the invention are 90%, 95%, 97.5%, 98%, 99%, 99.5%, 99.9% and 99.99%, while preferred p values are 0.1, 0.05, 0.025, 0.02, 0.01, 0.005, 0.001, and 0.0001. For example, the expression level of the at least one marker is indicative for the prediction and/or said prognosis and/or outcome compared to the expression level of a reference value at a p-value equal or below 0.05, preferably 0.01, more preferably 0.001 and even more preferably below 0.0001.

The present invention also relates to the use of the method for predicting a response or resistance to and/or a benefit from a treatment with the CDK4/6 inhibitor therapy in a subject suffering from a neoplastic disease. Equally, the present invention relates to the use of the method for predicting the outcome of a treatment with the CDK4/6 inhibitor therapy in a subject suffering from a neoplastic disease.

As mentioned herein above, in addition to the expression level of the at least one marker, further parameters of the subject may be determined. As used herein, a parameter is a characteristic, feature, or measurable factor that can help in defining a particular system. A parameter is an important element for health- and physiology-related assessments, such as a disease/disorder/clinical condition risk. Furthermore, a parameter is defined as a characteristic that is objectively measured and evaluated as an indicator of normal biological processes, pathogenic processes, or pharmacologic responses to a therapeutic intervention. For example, such further markers include but are not limited to age, sex, menopausal status, molecular subtype, estrogen-receptor (ER) status, progesterone-receptor (PR) status, human epidermal growth factor receptor 2 (HER2) status, Ki-67, tumor infiltrating lymphocytes, PD-1 activity, PD-L1 activity, histological tumor type, nodal status, metastases status, TNM staging, smoking history, ECOG performance status, Karnofsky status, tumor size at baseline and/or tumor grade at baseline. However, the method of the present invention does not need to rely on further parameters. In one embodiment, the method further comprises the determination of one more clinical parameters selected from the group consisting of pathological grading of the tumor, tumor size and nodal status. For example, the clinical parameter may be the pathological grading of the tumor at baseline and/or the tumor size at baseline and/or nodal status at baseline. The baseline refers to a value representing an initial level of a measurable quantity. The person skilled in the art knows that the baseline level may be determined before subject(s) are exposed to an environmental stimulus, receive an intervention such as a therapeutic treatment, or before a change of an environmental stimulus or a change in intervention such as a change in therapeutic treatment is induced. For example, the baseline may be determined before the start of the treatment of the subject(s) or before the start of a therapeutic intervention, such as the CDK4/6 inhibitor therapy, or before the start of another therapeutic intervention, such as a non-chemotherapy or chemotherapy combined with the CDK4/6 inhibitor therapy. The baseline level may be used for comparison with values representing response or resistance, benefit and/or outcome to an environmental stimulus and/or intervention, for example a particular treatment.

In other embodiments, a positive likelihood ratio, negative likelihood ratio, odds ratio, or hazard ratio is used as a measure of a test's ability to predict risk, response, outcome or benefit. In the case of a positive likelihood ratio, a value of 1 indicates that a positive result is equally likely among subjects in both the "good outcome" and "poor outcome" groups; a value greater than 1 indicates that a positive result is more likely in the diseased group; and a value less than 1 indicates that a positive result is more likely in the control group. In the case of a negative likelihood ratio, a value of 1 indicates that a negative result is equally likely among subjects in both the "diseased" and "control" groups; a value greater than 1 indicates that a negative result is more likely in the test group; and a value less than 1 indicates that a negative result is more likely in the control group. In certain preferred embodiments, markers and/or marker panels are preferably selected to exhibit a positive or negative likelihood ratio of at least about 1.5 or more or about 0.67 or less, more preferably at least about 2 or more or about 0.5 or less, still more preferably at least about 5 or more or about 0.2 or less, even more preferably at least about 10 or more or about 0.1 or less, and most preferably at least about 20 or more or about 0.05 or less. The term "about" in this context refers to +/−5% of a given measurement.

In the case of an odds ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group. In certain preferred embodiments, markers and/or marker panels are preferably selected to exhibit an odds ratio of at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less. The term "about" in this context refers to +/−5% of a given measurement. In the case of a hazard ratio, a value of 1 indicates that the relative risk of an endpoint (e.g. iDFS) is equal in both the "treatment" and "control/placebo" groups; a value greater than 1 indicates that the risk is higher in the diseased group; and a value less than 1 indicates that the risk is higher in the control group. In certain preferred embodiments, markers and/or marker panels are preferably selected to exhibit a hazard ratio of at least about 1.1 or more or about 0.91 or less, more preferably at least about 1.25 or more or about 0.8 or less, still more preferably at least about 1.5 or more or about 0.67 or less, even more preferably at least about 2 or more or about 0.5 or less, and most preferably at least about 2.5 or more or about 0.4 or less. The term "about" in this context refers to +/5% of a given measurement.

The sensitivity and specificity of a diagnostic and/or prognostic test depends on more than just the analytical "quality" of the test, they also depend on the definition of what constitutes an abnormal result. In practice, Receiver Operating Characteristic curves (ROC curves), are typically calculated by plotting the value of a variable versus its relative frequency in "normal" (i.e. apparently healthy) and "disease" populations (i.e. patients suffering from breast cancer). For any particular marker, a distribution of marker levels for subjects with and without a disease will likely overlap. Under such conditions, a test does not absolutely distinguish normal from disease with 100% accuracy, and the area of overlap indicates where the test cannot distinguish normal from disease. A threshold is selected, above which (or below which, depending on how a marker changes with the disease) the test is considered to be abnormal and below which the test is considered to be normal. The area under the ROC curve is a measure of the probability that the perceived measurement will allow correct identification of a condition. ROC curves can be used even when test results don't necessarily give an accurate number. As long as one can rank results, one can create a ROC curve. For example, results of a test on "disease" samples might be ranked according to degree (e.g. 1=low, 2=normal, and 3=high). This ranking can be correlated to results in the "normal" population, and a ROC curve created. These methods are well known in the art (See, e.g., Hanley et al. 1982. Radiology 143: 29-36). Preferably, ROC curves result in an AUC of greater than about 0.5, more preferably greater than about 0.7, still more preferably greater than about 0.8, even more preferably greater than about 0.85, and most preferably greater than about 0.9. The term "about" in this context refers to +/−5% of a given measurement.

The horizontal axis of the ROC curve represents (1-specificity), which increases with the rate of false positives. The vertical axis of the curve represents sensitivity, which increases with the rate of true positives. Thus, for a particular cut-off selected, the value of (1-specificity) may be determined, and a corresponding sensitivity may be obtained. The area under the ROC curve is a measure of the probability that the measured marker level will allow correct identification of a disease or condition. Thus, the area under the ROC curve can be used to determine the effectiveness of the test.

Suitable threshold levels for the stratification of subjects into different groups (categories; e.g. subjects that are to be treated with CDK4/6 inhibitor and subjects which are not to be treated with a CDK4/6 inhibitor) have to be determined for each particular combination of a marker level, further markers and/or parameters, medication and disease. This can e.g. be done by grouping a reference population of patients according to their marker level into certain quantiles, e.g. quartiles, quintiles or even according to suitable percentiles. For each of the quantiles or groups above and below certain percentiles, hazard ratios can be calculated comparing the risk for a particular (adverse) outcome, i.e. an "unfavourable effect", e.g. in terms of survival rate, between those patients who have received a certain medication and those who did not. In such a scenario, a hazard ratio (HR) above 1 indicates a higher risk for an adverse outcome for the patients who have received a treatment than for patients who did not. A HR below 1 indicates beneficial effects of a certain treatment in the group of patients. A HR around 1 (e.g. +/−0.1) indicates no elevated risk but also no benefit from medication for the particular group of patients. By comparison of the HR between certain quantiles of patients with each other and with the HR of the overall population of patients, it is possible to identify those quantiles of patients who have an elevated risk and those who benefit from medication and thereby stratify subjects according to the present invention.

As used herein, the term "score" refers to a numeric value derived from the mathematical combination of the expression level of at least two markers and/or the combination of the expression level of the at least one marker and at least one further parameter. As used herein, the term "combination" or "combining" refers to deriving a numeric value from a determined expression level of at least two marker, or from a determined expression level of at least one marker and at least one further parameter. An algorithm may be applied to one or more expression level of at least two marker or the expression level of at least one marker and at least one further parameter to obtain the numerical value or the score. An "algorithm" is a process that performs some sequence of operations to produce information.

Combining these expression levels and/or parameters can be accomplished for example by multiplying each expression level and/or parameter with a defined and specified coefficient and summing up such products to yield a score. The score may be also derived from expression levels together with further parameter(s) like lymph node status or tumor grading as such variables can also be coded as numbers in an equation. The score may be used on a continuous scale to predict the response or resistance and/or benefit and/or the outcome of the subject to the treatment with an immune checkpoint inhibitor. Cut-off values may be applied to distinguish clinical relevant subgroups, i.e. "responder", "non-responder", "positive outcome" and "negative outcome".

Cutoff values for such scores can be determined in the same way as cut-off values for conventional diagnostic markers and are well known to those skilled in the art. For example, one way of determining such cut-off value is to construct a receiver-operator curve (ROC curve) on the basis of all conceivable cut-off values, determining the single point on the ROC curve with the lowest proximity to the upper left corner (0/1) in the ROC plot. Typically, most of the time cut-off values will be determined by less formalized procedures by choosing the combination of sensitivity and specify determined by such cut-off value providing the most beneficial medical information to the problem investigated.

A "discriminant function" is a function of a set of variables used to classify an object or event. A discriminant function thus allows classification of a patient, samples or event into a category or a plurality of categories according to data or parameters available from said subject, sample or event. Such classification is a standard instrument of statistical analysis well known to the skilled person. For example, the subject may be classified to be indicative for the prediction and/or prognosis of group i) to iv):

i) an increased likelihood of the patient to respond and/or benefit from a CDK4/6 inhibitor treatment;
ii) an increased likelihood of the patient not to respond and/or benefit to a CDK4/6 inhibitor treatment;
iii) an increased likelihood of the patient to have a good outcome after a CDK4/6 inhibitor treatment;
iv) an increased likelihood of the patient have a poor outcome after a CDK4/6 inhibitor treatment.

Classification is not limited to these categories, but may also be performed into a plurality of categories, such as "responder" and "good outcome" or grading or the like. Classification shall also be understood in a wider sense as a discriminating score, where e.g. a higher score represents a higher likelihood of distant metastasis, e.g. the (overall) risk of a distant metastasis. Examples for discriminant functions which allow a classification include, but are not limited to functions defined by support vector machines (SVM), k-nearest neighbors (kNN), (naive) Bayes models, linear regression models or piecewise defined functions such as, for example, in subgroup discovery, in decision trees, in logical analysis of data (LAD) and the like. In a wider sense, continuous score values of mathematical methods or algorithms, such as correlation coefficients, projections, support vector machine scores, other similarity-based methods, combinations of these and the like are examples for illustrative purpose. For example, the expression level of each of said at least one marker comprises combining the expression level of each of the at least one marker with a coefficient, wherein the coefficient is indicative for the prognosis and/or prediction.

In one embodiment, the at least one marker is substituted by at least one substitute marker, wherein the expression level of the substitute marker correlates with the expression level of the at least one marker. The decision whether the at least one marker may be substitute with a substitute marker may be determined by the Pearson correlation coefficient. The application of Pearson's correlation coefficient is common to statistical sampling methods, and it may be used to determine the correlation of two variables. The Pearson coefficient may vary between −1 and +1. A coefficient of 0 indicates that neither of the two variables can be predicted from the other by a linear equation, while a correlation of +1 or −1 indicates that one variable may be perfectly predicted by a linear function of the other. A more detailed discussion of the Pearson coefficient may be found in McGraw-Hill Encyclopedia of Science and Technology, 6th Edition, Vol. 17. For example, the substitute marker correlates with the at least one marker by an absolute value of the Pearson correlation coefficient of at least |0.4|, preferably at least |0.6|, more preferably of at least |0.8|.

The present invention also relates to kits and the use of kits for assessing the likelihood whether a patient suffering from a neoplastic disease, in particular breast cancer, will benefit from and/or respond to or be resistant to a CDK4/6 inhibitor treatment. The kit may comprise one or more detection reagents for determining the level of the expression level of the at least one marker and reference data including the reference level of the at least one marker, optionally wherein said detection reagents comprise at least a pair of oligonucleotides capable of specifically binding to the at least one marker. As used herein, the term "primer" refers to the ordinary meaning of this term which is well known to the person skilled in the art of molecular biology. Primers shall be understood as being polynucleotide molecules having a sequence identical, complementary, homologous, or homologous to the complement of the regions of a target molecule, which is to be detected or quantified, e.g. the at least one marker.

All patent and non-patent documents cited herein are hereby incorporated by reference in their entirety.

Particular Items of the Present Invention

In particular aspects, the invention relates to the following items:

1. A method for predicting a response or resistance to and/or a benefit from treatment with an inhibitor of cyclin-dependent kinases 4 (CDK4/6 inhibitor) in a subject suffering from a neoplastic disease, comprising the step of:
   determining in a sample obtained from said subject the expression level of at least one marker selected from the group consisting of Programmed death-ligand 1 (PD-L1), Desmoglein 3 (DSG3), Intraflagellar Transport Protein 52 (IFT52), genes associated with multidrug resistance, and genes associated with SUMOylation,
   wherein the expression level of the at least one marker is indicative for predicting the response or resistance to and/or the benefit from the treatment with the CDK4/6 inhibitor in said subject.
2. The method of item 1, wherein
   (i) the genes associated with multidrug resistance are selected from the group consisting of ATP-binding Cassette Sub-Family B Member 6, mitochondrial (ABCB6), Multidrug resistance-associated protein 1 (ABCC1), ATP-binding Cassette Sub-family A Member 5 (ABCA5), ATP-binding Cassette Sub-family C Member 6 (ABCC6), ATP-binding Cassette transporter Sub-family C Member 11 (ABCC11), and ATP Binding Cassette Subfamily C Member 12 (ABCC12), and/or
   (ii) the genes associated with SUMOylation are selected form the group consisting of Protein Inhibitor of Activated STAT 2 (PIAS2), Dual specificity mitogen-activated protein kinase kinase 6 (MAP2K6), Conserved Helix-Loop-Helix Ubiquitous Kinase (CHUK), Small ubiquitin-related modifier 1 (SUMO1), G/T mismatch-specific thymine DNA glycosylase (TDG), Aurora Kinase A (AURKA), Structural maintenance of chromosomes protein 3 (SMC3), Inhibitor of Nuclear Factor Kappa-B Kinase Subunit gamma (IKBKG) and Xeroderma pigmentosum, complementation group C (XPC).
3. The method of item 1 or 2, wherein the at least one marker is selected from the group consisting of PD-L1, PIAS2, MAP2K6, DSG3, ABCC12 and IFT52.
4. The method of items 1 to 3, wherein the marker is PD-L1.
5. The method of items 1 to 3, wherein a panel of two or more markers is determined, e.g. at least two, three, four or five markers selected from the group consisting of PD-L1, PIAS2, MAP2K6, DSG3, ABCC12 and IFT52 is determined in said sample.
6. The method of items 1 to 4, wherein a panel of two or more markers is determined, e.g. at least two, three, four, five, six, seven, eight, nine, ten, eleven, twelve or thirteen or all markers selected from the group consisting of PD-L1, ABCA5, ABCB6, ABCC1, ABCC12, CALML3, CCL13, DSG3, HPSE, IL1RAP, MAP2K6, NF2, PEX12 and PIAS2 is determined in said sample.
7. The method of items 1 to 3, wherein a panel of two or more markers is determined, e.g. at least two, three, four, five, six, seven, eight, nine, ten, eleven or twelve or all markers selected from the group consisting of ABCA5, ABCB6, ABCC1, ABCC12, CALML3, CCL13, DSG3, HPSE, IL1RAP, MAP2K6, NF2, PEX12 and PIAS2 is determined in said sample.
8. The method of item 1 to 7, wherein the neoplastic disease is a solid tumor.
9. The method of items 1 to 7, wherein the neoplastic disease is a disease selected from the group consisting of breast cancer, head and neck cancer, small cell lung cancer (SCLC), non-small cell lung cancer (NSCLC), recurring brain metastasis, squamous cell carcinoma and central nervous system tumor.
10. The method of item 9, wherein the neoplastic disease is breast cancer.
11. The method of item 10, wherein the breast cancer is primary breast cancer.

12. The method of item 9, wherein the breast cancer is hormone receptor (HR)-positive, human epidermal growth factor receptor 2 (HER2)-negative either primary diagnosed or locally advanced or metastatic breast cancer.
13. The method of items 1 to 8, wherein the CDK4/6 inhibitor is selected from the group consisting of palbociclib, ribociclib, abemaciclib and trilaciclib
14. The method of item 13, wherein the CDK4/6 inhibitor is palbociclib.
15. The method of items 1 to 14, wherein the sample is a tumor tissue sample.
16. The method of items 1 to 14, wherein the sample is a primary tumor tissue sample.
17. The method of item 16, wherein the sample is a core biopsy sample.
18. The method of item 17, wherein the sample is a core biopsy sample from a primary tumor before any treatment.
19. The method of items 15 to 18, wherein the sample is a post-surgical residual tumor tissue sample or a post-surgical lymph node sample.
20. The method of item 15, wherein the sample is a post-surgical and post-chemotherapy tissue sample.
21. The method of items 15 to 20, wherein the sample is a formalin-fixed, paraffin-embedded (FFPE) tumor tissue sample.
22. The method of items 1 to 21, wherein the expression level is determined at mRNA or at protein level.
23. The method of item 22, wherein the expression level is determined at mRNA level.
24. The method of item 23, wherein the expression level is determined in a hybridization-based method, a PCR based method, a microarray-based method, a sequencing and/or next generation sequencing method.
25. The method of item 22, wherein the expression level is determined at protein level.
26. The method of item 25, wherein the expression level is determined in an immunohistochemistry (IHC) assay.
27. The method of item 26, wherein the marker is PD-L1.
28. The method of any of the preceding items, wherein the response, resistance and/or benefit is the invasive disease-free survival (iDFS), distant-disease-free survival (DDFS), pathological complete response (pCR), loco-regional recurrence free interval (LRRFI), loco-regional invasive recurrence free interval (LRIRFI), disease free survival (DFS), event free survival (EFS) and/or overall survival (OS).
29. The method of any of the preceding items, wherein the marker is selected from the group consisting of PD-L1, PIAS2, MAP2K6, DSG3, IFT52, ABCB6, ABCC1, ABCA5, ABCC6, ABCC11, ABCC12, CHUK, SUM01, TDG, AURKA, SMC3 and IKBKG, and wherein a higher expression is associated with a higher likelihood of benefit from the CDK4/6 inhibitor, and a lower expression is associated with a lower benefit, no benefit or a disadvantage from the CDK4/6 inhibitor.
30. The method of any of the preceding items, wherein the marker is XPC, and wherein a lower expression is associated with a higher likelihood of benefit from the CDK4/6 inhibitor, and a higher expression is associated with a lower benefit, no benefit or a disadvantage from the CDK4/6 inhibitor.
31. The method of any of the preceding items, wherein the method comprises comparing the expression level of each of said at least one marker to a predetermined reference level.
32. The method of item 31, wherein the marker is selected from the group consisting of PD-L1, PIAS2, MAP2K6, DSG3, IFT52, ABCB6, ABCC1, ABCA5, ABCC6, ABCC11, ABCC12, CHUK, SUMO1, TDG, AURKA, SMC3 and IKBKG, and wherein patients with expression level above the reference level have a high likelihood of benefit from the CDK4/6 inhibitor, and wherein patients with an expression level below the reference level have no benefit or a disadvantage from the CDK4/6 inhibitor.
33. The method of item 31, wherein the marker is XPC, and wherein patients with expression level below the reference level have a high likelihood of benefit from the CDK4/6 inhibitor, and wherein patients with an expression level above the reference level have no benefit or a disadvantage from the CDK4/6 inhibitor.
34. The method of any of the preceding items, wherein the method further comprises the determination of one or more clinical parameters selected from the group consisting of pathological grading of the tumor, tumor size, nodal status, proliferation (in particular Ki-67), and immune system markers (in particular lymphocytes).
35. The method of any of the preceding items, wherein the method further comprises the determination of the expression level of Cyclin E1 (CCNE1; also known as G1/S-specific cyclin-E1).
36. A CDK4/6 inhibitor for use in the treatment of neoplastic disease in a subject, wherein the subject has been determined to have a benefit from treatment with a CDK4/6 inhibitor in a method according to items 1 to 35.
37. A CDK4/6 inhibitor for use in the treatment of neoplastic disease in a subject, wherein the subject has been determined to have an increased expression level of at least one marker selected from the group consisting of PD-L1, PIAS2, MAP2K6, DSG3, ABCC12, IFT52, ABCB6, ABCC1, ABCA5, ABCC6, ABCC11, CHUK, SUM01, TDG, AURKA, SMC3 and IKBKG and/or a decreased expression level of XPC, in a sample of said subject.
38. The CDK4/6 inhibitor for use according to item 37, wherein the marker is increased or decreased, respectively, as compared to a predetermined reference level.
39. The CDK4/6 inhibitor for use according to items 37 and 38, wherein the marker is selected from the group consisting of PD-L1, PIAS2, MAP2K6, DSG3, ABCC12 and IFT52.
40. The CDK4/6 inhibitor for use according to item 39, wherein the marker is PD-L1.
41. The CDK4/6 inhibitor for use according to items 37 to 40, wherein the CDK4/6 inhibitor is selected from the group consisting of palbociclib, ribociclib, abemaciclib and trilaciclib.
42. The CDK4/6 inhibitor for use according to item 41, wherein the CDK4/6 inhibitor is palbociclib.
43. The CDK4/6 inhibitor for use according to items 37 to 42, wherein the neoplastic disease is a disease selected form the group consisting of breast cancer, head and neck cancer, non-small cell lung cancer, recurring brain metastasis, squamous cell carcinoma and central nervous system tumor.

44. The CDK4/6 inhibitor for use according to items 37 to 43, wherein the neoplastic disease is breast cancer.
45. The CDK4/6 inhibitor for use according to item 44, wherein the breast cancer is hormone receptor (HR)-positive, human epidermal growth factor receptor 2 (HER2)-negative breast cancer.
46. The CDK4/6 inhibitor for use according to items 37 to 45, wherein the treatment is after neoadjuvant chemotherapy and surgery.
47. The CDK4/6 inhibitor for use according to items 37 to 46, wherein the treatment is combined with an endocrine therapy such as an aromatase inhibitor, tamoxifen, fulvestrant, or an luteinizing hormone-releasing hormone (LHRH) agonist or analogue.
48. The CDK4/6 inhibitor for use according to items 37 to 47, wherein the treatment is combined with the administration of fulvestrant and wherein the subject is a female patient suffering from hormone receptor (HR)-positive, human epidermal growth factor receptor 2 (HER2)-negative locally advanced or metastatic breast cancer who has received prior endocrine therapy.

EXAMPLES

Example 1

Overview of Clinical Study

The data underlying the present invention were obtained in the context of the PENELOPE$^B$ study (NCT01864746).

PENELOPE$^B$ is a randomized, double-blind, placebo-controlled Phase 3 study comparing one year of palbociclib plus at least five years of standard adjuvant endocrine therapy to placebo plus at least five years of standard adjuvant endocrine therapy in 1,250 women with HR+, HER2− eBC at high risk of recurrence who have residual invasive disease after completing neoadjuvant chemotherapy. Patients in the trial scored 3 or higher (or 2 if there were lymph node metastases at the time of surgery) on the clinical-pathologic stage—estrogen/grade (CPS-EG). The CPS-EG is a validated risk assessment tool combining: clinical stage before neoadjuvant treatment, pathological stage after neoadjuvant treatment, grading and estrogen-receptor status.

More than 190 clinical sites in 12 countries around the globe participated in PENELOPE-B. The study opened in November 2013 and closed recruitment on Dec. 31, 2017.

Gene Expression Analysis

RNA was extracted from post-surgical residual tumor tissue of patients from the Penelope$^B$ study (GBG 78) and quantified using the HTG EdgeSeq Oncology Biomarker Panel (HTG Molecular Diagnostics Inc.) resulting in a so-called count value for each of the 2559 genes in the assay. Quality control measures were performed as described by the manufacturer. For 906 patients HTG measurements were successfully performed and passed said quality controls.

Statistical Analyses

Gene expressions were normalized for statistical analyses by the CPM (counts per million) method and application of a lower bound of 3 for each patient separately.

Let $x_i$ denote the count of gene i. The total count X is the sum of the counts of all 2559 genes of said assay (negative and positive controls are excluded; housekeeping genes are included).

$$X := \sum_{i=1}^{2559} x_i$$

Let $\xi_i$ be the CPM-transformed expression value for gene i; it is calculated as:

$$\xi_i := \log_2\left(1{,}000{,}000 \cdot \frac{x_i + 0.5}{X + 1}\right),\quad i = 1, \ldots, 2559.$$

To improve reproducibility of measurements a lower bound of 3 on CPM values was introduced:

$$\tilde{\xi}_i := \max\{3, \xi_i\} = \max\left\{3,\ \log_2\left(1{,}000{,}000 \cdot \frac{x_i + 0.5}{X + 1}\right)\right\},\quad i = 1, \ldots, 2559$$

where $\tilde{\xi}_i$ is the finally normalized gene expression value for gene i.

Results

Analysis results related to the ability of gene expressions to predict a potential benefit from palbociclib: For each gene results of a bivariate Cox regression model for endpoint iDFS with the normalized gene expression, the treatment arm and their interaction as independent terms are presented. Five of the six genes with smallest p-value for interaction are highly correlated to each other: PIAS2, MAP2K6, DSG3, ABCC12 and IFT52. The following Table 1 shows the pairwise Spearman correlation coefficients for these five genes:

TABLE 1

Pairwise Spearman correlation coefficients for five genes

| Spearman correlation | PIAS2 | MAP2K6 | DSG3 | ABCC12 | IFT52 |
|---|---|---|---|---|---|
| PIAS2 | 1.00 | 0.41 | 0.35 | 0.27 | 0.40 |
| MAP2K6 | 0.41 | 1.00 | 0.58 | 0.52 | 0.40 |
| DSG3 | 0.35 | 0.58 | 1.00 | 0.60 | 0.37 |
| ABCC12 | 0.27 | 0.52 | 0.60 | 1.00 | 0.33 |
| IFT52 | 0.40 | 0.40 | 0.37 | 0.33 | 1.00 |

For each gene of the HTG assay a bivariate Cox regression model was created to examine the interaction between gene expression and treatment arm with respect to endpoint iDFS. Each regression model was calculated based on 906 patients from the Penelope$^B$ study. Independent terms were the normalized continuous gene expression value, the treatment arm as a binary variable and their interaction. The following Table 2 shows genes with small p-values for interaction, wherein genes were selected into gene sets based on different criteria. Criteria were the said p-value for interaction and biological properties such as function and pathways.

TABLE 2

Gene expression of certain biomarkers and their correlation to the outcome in placebo and palbociclib treated patients. HR: hazard ratio; CI: confidence interval.

| gene set | gene | p-value for interaction | HR (in placebo, 95% CI) | HR (in palbociclib, 95% CI) |
|---|---|---|---|---|
| PD-L1 | CD274 | 0.0367 | 0.97 (0.80-1.18) | 0.73 (0.60-0.88) |
| smallest p-value for interaction | PIAS2 | 0.0002 | 1.73 (1.18-2.54) | 0.65 (0.46-0.92) |
| | MAP2K6 | 0.0005 | 1.26 (0.97-1.63) | 0.68 (0.54-0.86) |
| | DSG3 | 0.0006 | 1.26 (1.10-1.45) | 0.87 (0.75-1.02) |

TABLE 2-continued

Gene expression of certain biomarkers and their correlation to the outcome in placebo and palbociclib treated patients. HR: hazard ratio; CI: confidence interval.

| gene set | gene | p-value for interaction | HR (in placebo, 95% CI) | HR (in palbociclib, 95% CI) |
|---|---|---|---|---|
| | ABCC12 | 0.0013 | 1.12 (0.99-1.28) | 0.83 (0.72-0.95) |
| | IFT52 | 0.0014 | 1.72 (1.17-2.52) | 0.69 (0.46-1.04) |
| multidrug resistance genes | ABCC12 | 0.0013 | 1.12 (0.99-1.28) | 0.83 (0.72-0.95) |
| | ABCB6 | 0.0038 | 1.22 (0.92-1.62) | 0.69 (0.53-0.90) |
| | ABCC1 | 0.0046 | 1.50 (1.01-2.23) | 0.73 (0.54-0.99) |
| | ABCA5 | 0.0093 | 1.04 (0.81-1.32) | 0.66 (0.52-0.84) |
| | ABCC6 | 0.0472 | 1.05 (0.89-1.24) | 0.83 (0.70-0.98) |
| | ABCC11 | 0.0584 | 1.03 (0.91-1.15) | 0.86 (0.75-0.99) |
| SUMO pathway, SUMOylation | PIAS2 | 0.0002 | 1.73 (1.18-2.54) | 0.65 (0.46-0.92) |
| | MAP2K6 | 0.0005 | 1.26 (0.97-1.63) | 0.68 (0.54-0.86) |
| | CHUK | 0.0096 | 1.15 (0.78-1.70) | 0.56 (0.38-0.82) |
| | SUMO1 | 0.0302 | 2.13 (1.35-3.36) | 1.06 (0.69-1.64) |
| | TDG | 0.0568 | 2.16 (1.44-3.22) | 1.24 (0.82-1.86) |
| | AURKA | 0.0595 | 1.43 (1.18-1.73) | 1.10 (0.91-1.33) |
| | SMC3 | 0.0644 | 1.39 (0.92-2.09) | 0.81 (0.54-1.21) |
| | IKBKG | 0.0660 | 1.06 (0.86-1.30) | 0.79 (0.63-1.00) |
| SUMO pathway, inverse expression | XPC | 0.0434 | 0.58 (0.41-0.82) | 0.94 (0.69-1.28) |
| | CCNE1 | 0.0437 | 1.32 (1.17-1.49) | 1.08 (0.93-1.26) |

The rightmost columns show the unit hazard ratios of the normalized gene expression in the placebo arm and in the palbociclib arm, respectively; the p-value for interaction indicates how different these two hazard ratios are. Since all p-values are small each of the genes can be utilized to decide whether a patient will benefit from palbocliclib, because overall no significant difference between the treatment arms were found (palbociclib vs. placebo: HR=0.89 (0.69-1.16), n=906).

High CD274 (PD-L1) expression indicates a good prognosis with palbociclib (HR<1), but is not prognostic in the placebo arm (HR≈1). Therefore patients with high PD-L1 will benefit from palbociclib while patients with low PD-L1 will not.

Each gene from the $2^{nd}$ gene set also indicates a good prognosis with palbociclib (HR<1). In addition, it indicates a bad prognosis in the placebo arm (HR>1). Again, patients with high expression will benefit from palbociclib while patients with low expression will not.

Genes from the multidrug resistance group again indicate a good prognosis with palbociclib (HR<1) and no or bad prognosis in the placebo arm. Again, patients with high expression will benefit from palbociclib while patients with low expression will not.

Prognostic and predictive properties of genes from the SUMO group superpose differently. But again, patients with high expression will benefit from palbociclib while patients with low expression will not.

The XPC gene indicates good prognosis in the placebo arm and is not prognostic with palbociclib. Therefore, this gene differs from all other genes listed in the direction of interaction. Patients with low XPC expression will benefit from palbociclib while patients with high XPC expression will not.

CCNE1 indicates bad prognosis in the placebo arm and is not prognostic with palbociclib. Patients with high CCNE1 expression will benefit from palbociclib while patients with low CCNE1 expression will not.

Example 2

For the patients from example 1 some clinical variables are also available. The aim of this example is to demonstrate how to construct a multivariable algorithm combining a gene expression variable and clinical variables into a score being predictive for the response to palbociclib.

The variables examined for this example are shown in Table 3:

TABLE 3

| Variable | Values |
|---|---|
| CD274 | normalized gene expression, continuous |
| age | >50 years vs <=50 years, at time of diagnosis |
| Ki67 | >15% vs <=15%, IHC |
| ypN | ypN2-3 vs ypN0-1 |
| risk_status | CPS-EG status >=3 vs CPS-EG status = 2 and ypN+ |
| cT | cT3-4 vs cT1-2, at time of diagnosis |
| ypT | ypT3-4 vs ypT0-2 |
| grade | G3 vs G1-2 |

All clinical variables are binary; the first category is the category of interest, the second is the reference category for the coefficients and hazard ratios below.

A Cox regression model with respect to iDFS was created containing the following terms:

variable arm (palbociclib vs placebo) (1 term), each variable from the table above (8 terms), and an interaction term for each variable from the table above with the variable arm (8 terms).

The Wald p-values for the interaction terms were as shown in Table 4:

TABLE 4

| Variable | p-value of interaction term with variable arm |
|---|---|
| CD274 | 0.0433 |
| age | 0.2569 |
| Ki67 | 0.6850 |
| ypN | 0.7413 |
| risk_status | 0.9798 |
| CT | 0.4970 |
| ypT | 0.0670 |
| grade | 0.5987 |

To keep the algorithm simple only variables contributing significantly were considered. Requiring a p-value<0.2 for the variable, only CD274 and ypT contribute.

The reduced Cox regression model is shown in Table 5.

TABLE 5

| Variable | coefficient | standard deviation of coefficient | p-value |
|---|---|---|---|
| arm | 1.5173 | 0.8269 | 0.0665 |
| CD274 | −0.0491 | 0.0998 | 0.6230 |
| ypT | 0.6527 | 0.2030 | 0.0013 |
| interaction of arm and CD274 | −0.2630 | 0.1397 | 0.0597 |
| interaction of arm and ypT | −0.3874 | 0.2967 | 0.1916 |

A new variable called score2 can now be defined using the coefficients of the interaction terms:

$$score2:=0.2630*CD274, \text{ if } ypT0\text{-}2$$

$$score2:=0.2630*CD274+0.3874, \text{ if } ypT3\text{-}4$$

The signs of the coefficients have been switched, so that higher score2 values indicate higher benefit from palbociclib—the same as with CD274.

The performance of the combined score is now superior compared to both variables individually; see Table 6:

TABLE 6

| variable | p-value for interaction | HR (in placebo, 95% CI) | HR (in palbociclib, 95% CI) |
|---|---|---|---|
| score2 | 0.0148 | 1.55 (0.84-2.85) | 0.50 (0.26-0.98) |
| CD274 | 0.0367 | 0.97 (0.80-1.18) | 0.73 (0.60-0.88) |
| ypT | 0.2607 | 1.90 (1.28-2.83) | 1.37 (0.90-2.08) |

Example 3

In example 2 different variables were combined by Cox regression coefficients. If variables highly correlate to each other more robust methods for combination may be superior. Example 3 defines a variable score3 as the average of the five claimed genes with smallest p-values for interaction.

score3:=(PIAS2+MAP2K6+DSG3+ABCC12+IFT52)/5

This combined score is superior to each single gene, because its p-value based on the same patients is smaller; see Table 7:

TABLE 7

| gene | p-value for interaction | HR (in placebo, 95% CI) | HR (in palbociclib, 95% CI) |
|---|---|---|---|
| score3 | 0.0000075 | 1.65 (1.22-2.24) | 0.64 (0.49-0.85) |
| PIAS2 | 0.0002 | 1.73 (1.18-2.54) | 0.65 (0.46-0.92) |
| MAP2K6 | 0.0005 | 1.26 (0.97-1.63) | 0.68 (0.54-0.86) |
| DSG3 | 0.0006 | 1.26 (1.10-1.45) | 0.87 (0.75-1.02) |
| ABCC12 | 0.0013 | 1.12 (0.99-1.28) | 0.83 (0.72-0.95) |
| IFT52 | 0.0014 | 1.72 (1.17-2.52) | 0.69 (0.46-1.04) |

Variable score3 can further be dichotomized into a binary variable score3dich, where the median in the Penelope study population is used as cutoff. A respective Cox model for the interaction of arm and score3dich results in a p-value for the interaction of 0.0002 and has the following hazard ratios:

TABLE 8

| subgroup | variable and categories | HR (95% CI) |
|---|---|---|
| placebo arm | score3dich (high vs low) | 1.51 (1.04-2.18) |
| palbociclib arm | score3dich (high vs low) | 0.56 (0.38-0.82) |
| score3dich low | arm (palbociclib vs placebo) | 1.45 (1.00-2.09) |
| score3dich high | arm (palbociclib vs placebo) | 0.54 (0.37-0.79) |

Based on this dichotomized variable patients with high score have significant benefit from palbociclib while patients with low score have worse iDFS with palbociclib compared to placebo.

Example 4

A marker panel (a "signature") called "Signature1" was constructed from HTG gene expression data and clinical data of 782 patients from the Penelope$^B$ study (see Example 1). The construction consisted of the following steps:

1) For each gene of the HTG panel a Cox regression model for endpoint iDFS with independent terms gene expression, treatment arm and their interaction was constructed. The 20 genes with smallest p-values for the interaction were selected.

2) For each gene from step 1) the technical eligibility for measurement was evaluated. Genes were excluded if their normalized gene expression
   a. had a standard deviation within the cohort of 0.5 or less, or
   b. was below the lower bound of 3 for 10% or more patients.

According to these criteria 5 of the 20 genes from step 1 were excluded. The remaining gene showed an approximately normal distribution within the cohort.

3) Since steps 4) and 5) are very sensitive to outliers, extreme expression values were adjusted. First, a lower and an upper limit for the univariable distribution of each gene was defined as median +/−3*mad (median absolute deviation). Second, gene expression values outside these limits were adjusted to the respective limit. In the cohort of 782 patients the gene expression value was adjusted to the lower limit for between 0 and 16 patients, and to the upper limit for between 0 and 8 patients.

4) The correlation between genes was analyzed by hierarchical clustering and analysis of the Pearson correlation coefficient matrix based on graphical methods. Two genes were only weakly correlated to the others and each other and therefore omitted. The remaining genes were correlated to each other, and no subcluster structure was observed.

5) A PCA (principal component analysis) was performed based on the 13 genes from step 4) after z-transformation of the normalized expression values. Again, no subcluster structure in the genes was found. The first principal component explained most of the variance; the remaining principal components contributed less in total.

The Signature 1 score was calculated as a linear combination of the expression of the 13 genes of step 5) where each linear coefficient was defined as the ratio of the coefficient of the first principal component and the standard deviation of the gene expression within the cohort. The following Table 9 shows these numbers:

TABLE 9

| gene | first principal component | standard deviation in cohort | Signature 1 coefficient |
|---|---|---|---|
| ABCA5 | 0.218 | 0.719 | 0.30 |
| ABCB6 | 0.285 | 0.677 | 0.42 |
| ABCC1 | 0.154 | 0.444 | 0.35 |
| ABCC12 | 0.283 | 1.336 | 0.21 |
| CALML3 | 0.263 | 1.237 | 0.21 |
| CCL13 | 0.309 | 1.106 | 0.28 |
| DSG3 | 0.322 | 1.129 | 0.28 |
| HPSE | 0.319 | 0.876 | 0.36 |
| IL1RAP | 0.327 | 0.702 | 0.47 |
| MAP2K6 | 0.305 | 0.710 | 0.43 |
| NF2 | 0.197 | 0.480 | 0.41 |
| PEX12 | 0.347 | 0.809 | 0.43 |
| PIAS2 | 0.195 | 0.501 | 0.39 |

Thus, the Signature 1 score is calculated as $$\text{score1} := 0.30*ABCA5 + 0.42*ABCB6 + 0.35*ABCC1 + 0.21*ABCC12 + 0.21*CALML3 + 0.28*CCL13 + 0.28*DSG3 + 0.36*HPSE + 0.47*IL1RAP + 0.43*MAP2K6 + 0.41*NF2 + 0.43*PEX12 + 0.39*PIAS2$$

where each gene name represents its normalized (but not z-transformed) expression from the HTG assay.

Signature 1 as a continuous variable predicts the response to palbociclib in the Penelope cohort (training cohort). The following Table 10 shows the results from three different Cox regression models for endpoint iDFS. Model "bivar" has three independent terms: Signature1, treatment arm (palbociclib vs placebo) and their interaction. Models "multi1b" and "multi2b" have additional clinical covariables.

TABLE 10

| model | n | HR(in placebo, CI) | HR(in palbociclib, CI) | p |
|---|---|---|---|---|
| bivar | 782 | 1.13 (1.05-1.23) | 0.88 (0.82-0.95) | 4.696e−06 |
| multi1b | 770 | 1.14 (1.05-1.24) | 0.88 (0.81-0.94) | 2.842e−06 |
| multi2b | 782 | 1.15 (1.06-1.25) | 0.87 (0.81-0.94) | 8.359e−07 |

Column "n" shows the number of patients available for this model.

Column "HR(in placebo, CI)" shows the hazard ratio of iDFS related to a one-unit increase of variable score1 (Signature1) in the placebo arm (with 95% confidence interval). Column "HR(in palbociclib, CI)" shows the same for the palbociclib arm.

Column "p" shows the Wald p-value for the interaction term; these p-values are smaller than the corresponding p-values of each gene used to construct Signature1, thus Signature1 has superior predictive performance compared to the single genes.

Figure 2:
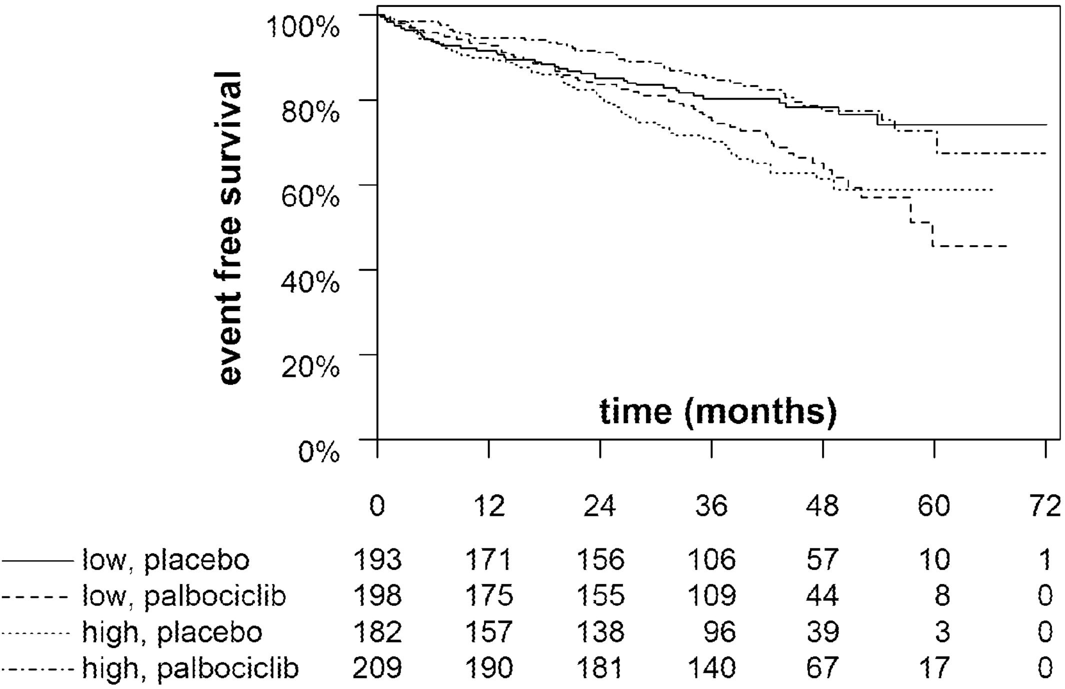
FIG. 2 shows a Kaplan-Meier plot for the "Signature 1" marker panel of Example 4.

FIG. 2 shows a Kaplan-Meier curve using the dichotomized Signature 1 with the median used as cutoff, separate Kaplan-Meier curves by Signature 1 (low vs high) and by arm are shown. It can be seen that patients with low (below median) Signature 1 score have fewer events in the placebo arm, but patients with high Signature 1 have fewer events in the palbociclib arm. Thus, Signature 1 can predict the favorable treatment arm.

The following Table 11 shows the Pearson correlation coefficients of the genes in Signature 1:

TABLE 11

| | ABCA5 | ABCB6 | ABCC1 | ABCC12 | CALML3 | CCL13 | DSG3 | HPSE | IL1RAP | MAP2K6 | NF2 | PEX12 | PIAS2 |
|---|---|---|---|---|---|---|---|---|---|---|---|---|---|
| ABCA5 | 1.00 | 0.34 | 0.27 | 0.26 | 0.29 | 0.29 | 0.33 | 0.28 | 0.40 | 0.57 | 0.38 | 0.44 | 0.50 |
| ABCB6 | 0.34 | 1.00 | 0.22 | 0.50 | 0.38 | 0.53 | 0.50 | 0.53 | 0.45 | 0.51 | 0.43 | 0.61 | 0.27 |
| ABCC1 | 0.27 | 0.22 | 1.00 | 0.14 | 0.18 | 0.19 | 0.24 | 0.31 | 0.41 | 0.29 | 0.37 | 0.29 | 0.36 |
| ABCC12 | 0.26 | 0.50 | 0.14 | 1.00 | 0.41 | 0.55 | 0.48 | 0.59 | 0.57 | 0.47 | 0.26 | 0.62 | 0.23 |
| CALML3 | 0.29 | 0.38 | 0.18 | 0.41 | 1.00 | 0.40 | 0.63 | 0.42 | 0.52 | 0.44 | 0.26 | 0.49 | 0.26 |
| CCL13 | 0.29 | 0.53 | 0.19 | 0.55 | 0.40 | 1.00 | 0.60 | 0.69 | 0.63 | 0.51 | 0.26 | 0.69 | 0.19 |
| DSG3 | 0.33 | 0.50 | 0.24 | 0.48 | 0.63 | 0.60 | 1.00 | 0.55 | 0.65 | 0.54 | 0.30 | 0.62 | 0.34 |
| HPSE | 0.28 | 0.53 | 0.31 | 0.59 | 0.42 | 0.69 | 0.55 | 1.00 | 0.70 | 0.55 | 0.33 | 0.71 | 0.25 |
| IL1RAP | 0.40 | 0.45 | 0.41 | 0.57 | 0.52 | 0.63 | 0.65 | 0.70 | 1.00 | 0.55 | 0.35 | 0.72 | 0.36 |
| MAP2K6 | 0.57 | 0.51 | 0.29 | 0.47 | 0.44 | 0.51 | 0.54 | 0.55 | 0.55 | 1.00 | 0.35 | 0.67 | 0.43 |
| NF2 | 0.38 | 0.43 | 0.37 | 0.26 | 0.26 | 0.26 | 0.30 | 0.33 | 0.35 | 0.35 | 1.00 | 0.38 | 0.40 |
| PEX12 | 0.44 | 0.61 | 0.29 | 0.62 | 0.49 | 0.69 | 0.62 | 0.71 | 0.72 | 0.67 | 0.38 | 1.00 | 0.41 |
| PIAS2 | 0.50 | 0.27 | 0.36 | 0.23 | 0.26 | 0.19 | 0.34 | 0.25 | 0.36 | 0.43 | 0.40 | 0.41 | 1.00 |

It can be seen that all correlations are positive and most are high. This means that each gene contributes in a similar way, each gene may be replaced by others, and thus single genes might be omitted with only small changes in Signature 1.

The contribution of each gene to Signature 1 is shown in Table 12 containing the Pearson correlation coefficients between Signature 1 and each of its genes:

TABLE 12

| gene | Pearson correlation coefficient |
|---|---|
| ABCA5 | 0.57 |
| ABCB6 | 0.71 |
| ABCC1 | 0.43 |
| ABCC12 | 0.70 |
| CALML3 | 0.64 |
| CCL13 | 0.76 |
| DSG3 | 0.78 |
| HPSE | 0.80 |
| IL1RAP | 0.83 |
| MAP2K6 | 0.77 |
| NF2 | 0.53 |
| PEX12 | 0.87 |
| PIAS2 | 0.52 |

Each gene contributes to Signature1 and the magnitude of contribution is similar between genes. Therefore, single genes may be omitted with only small changes in Signature1.

Conclusion: Omitting one or more genes from Signature) will result in an alternative signature which is still highly correlated to Signature1.

Figure 4:
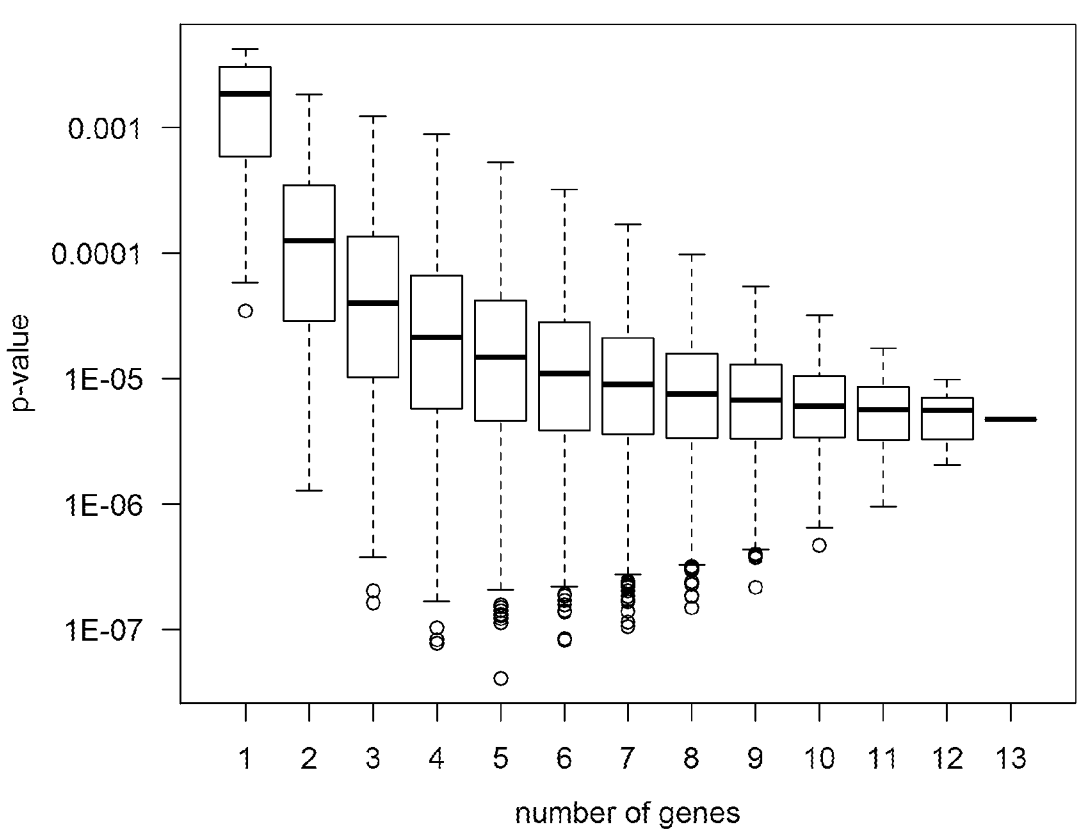
FIG. 4 shows a whisker-and-box plot for marker subsets from Signature 1 with the p-values of these interaction tests on the y-axis and the number of genes (i.e. subset size) on the x-axis.

All potential subsets of the genes in Signature 1 were created. For each such subset a signature was created using the linear coefficients from Signature1, and for each such subset signature a test for interaction with the treatment arm was performed. FIG. 4 shows a whisker-and-box plot with the p-values of these interaction tests on the y-axis and the number of genes (i.e. subset size) on the x-axis.

In FIG. 4, box "1" shows the distribution of the interaction p-values for the 13 single genes; box "13" shows the one and only p-value for Signature 1. It can be seen that the median p-value decreases if more genes are included in the signature, but the decrement becomes lower for more genes. This means that the number of 13 genes in Signature 1 is a good compromise between the predictive power on one hand the technical efforts for measurement on the other hand in a diagnostic assay. But it also means that fewer genes, e.g. 4, 6, or 10 may also be acceptable for routine diagnostics. For most subsets of genes such an alternative signature will have the same clinical properties and thus be the same invention. The best subset of genes seems to be the one with the smallest interaction p-value (although its selection would clearly be overfitting in the training cohort). This subset consists of the genes ABCC1, DSG3, MAP2K6, NF2, and PIAS2; using the same linear coefficients as for Signature 1 Cox model results are shown in Table 14:

TABLE 14

| model | n | HR(in placebo, CI) | HR(in palbociclib, CI) | p |
|---|---|---|---|---|
| bivar | 782 | 1.74 (1.37-2.22) | 0.73 (0.60-0.88) | 4.082e–08 |
| multi1b | 770 | 1.73 (1.34-2.23) | 0.71 (0.57-0.87) | 7.967e–08 |
| multi2b | 782 | 1.74 (1.36-2.23) | 0.71 (0.58-0.87) | 3.062e–08 |

Example 5

CD274 (PD-L1) surprisingly shows significant predictive properties in the luminal Penelope cohort. Table 15 shows the results of Cox regression models with respect to end-point iDFS:

TABLE 15

| model | n | HR(in placebo, CI) | HR(in palbociclib, CI) | p |
|---|---|---|---|---|
| bivar | 782 | 1.02 (0.83-1.26) | 0.73 (0.60-0.89) | 0.02392 |
| multi1b | 770 | 1.04 (0.84-1.28) | 0.73 (0.60-0.90) | 0.02182 |
| multi2b | 782 | 1.02 (0.83-1.26) | 0.72 (0.59-0.88) | 0.01833 |

The following Table 16 shows the Pearson correlation coefficient between CD274 (PD-L1) and each single gene from Signature 1 and the Signature 1 score as defined above.

TABLE 16

| | |
|---|---|
| ABCA5 | 0.32 |
| ABCB6 | 0.47 |
| ABCC1 | 0.29 |
| ABCC12 | 0.53 |
| CALML3 | 0.44 |
| CCL13 | 0.74 |
| DSG3 | 0.63 |
| HPSE | 0.75 |
| IL1RAP | 0.71 |
| MAP2K6 | 0.51 |
| NF2 | 0.28 |
| PEX12 | 0.70 |
| PIAS2 | 0.29 |
| score1 | 0.76 |

Hence, CD274 is highly correlated to Signature 1 and also to several of its member genes. Therefore, CD274 may be seen as a representative or surrogate for Signature 1. Based on this observation an alternative signature called Signature 2 was constructed: CD274 was added to the set of genes in Signature 1 and step 5 (PCA) of the construction was repeated. Again, no subcluster structure in the genes was found. The first principal component explained most of the variance; the remaining principal components contributed less in total. The Signature 2 score was calculated as a linear combination according to the following Table 17:

TABLE 17

| gene | first principal component | standard deviation in cohort | Signature1 coefficient |
|---|---|---|---|
| ABCA5 | 0.201 | 0.719 | 0.28 |
| ABCB6 | 0.267 | 0.677 | 0.39 |
| ABCC1 | 0.146 | 0.444 | 0.33 |
| ABCC12 | 0.269 | 1.336 | 0.20 |
| CALML3 | 0.248 | 1.237 | 0.20 |
| CCL13 | 0.301 | 1.106 | 0.27 |
| DSG3 | 0.307 | 1.129 | 0.27 |
| HPSE | 0.310 | 0.876 | 0.35 |
| IL1RAP | 0.315 | 0.702 | 0.45 |
| MAP2K6 | 0.286 | 0.710 | 0.40 |

TABLE 17-continued

| gene | first principal component | standard deviation in cohort | Signature1 coefficient |
|---|---|---|---|
| NF2 | 0.182 | 0.480 | 0.38 |
| PEX12 | 0.332 | 0.809 | 0.41 |
| PIAS2 | 0.181 | 0.501 | 0.36 |
| CD274 | 0.308 | 0.934 | 0.33 |

Thus, the Signature 2 score is calculated as $$\begin{aligned}score2 := {} & 0.28*ABCA5+0.39*ABCB6+\\ & 0.33*ABCC1+0.20*ABCC12+0.20*CALML3+0.27*CCL13+\\ & 0.27*DSG3+0.35*HPSE+0.45*IL1RAP+0.40*MAP2K6+\\ & 0.38*NF2+0.41*PEX12+0.36*PIAS2+0.33*CD274\end{aligned}$$

where each gene name represents its normalized (but not z-transformed) expression from the HTG assay.

Signature 2 as a continuous variable predicts the response to palbociclib in the Penelope cohort (training cohort). The following Table 18 shows the results from three different Cox regression models.

TABLE 18

| model | n | HR(in placebo, CI) | HR(in palbociclib, CI) | p |
|---|---|---|---|---|
| bivar | 782 | 1.12 (1.04-1.20) | 0.89 (0.83-0.95) | 1.039e–05 |
| multi1b | 770 | 1.12 (1.04-1.21) | 0.88 (0.82-0.95) | 6.798e–06 |
| multi2b | 782 | 1.13 (1.04-1.22) | 0.87 (0.81-0.94) | 2.247e–06 |

Although the p-values for Signature 2 are higher compared to Signature 1 they are still very significant. Since they relate to the training set, Signature 2 may be superior to Signature 1 in an independent validation cohort.

Figure 3:
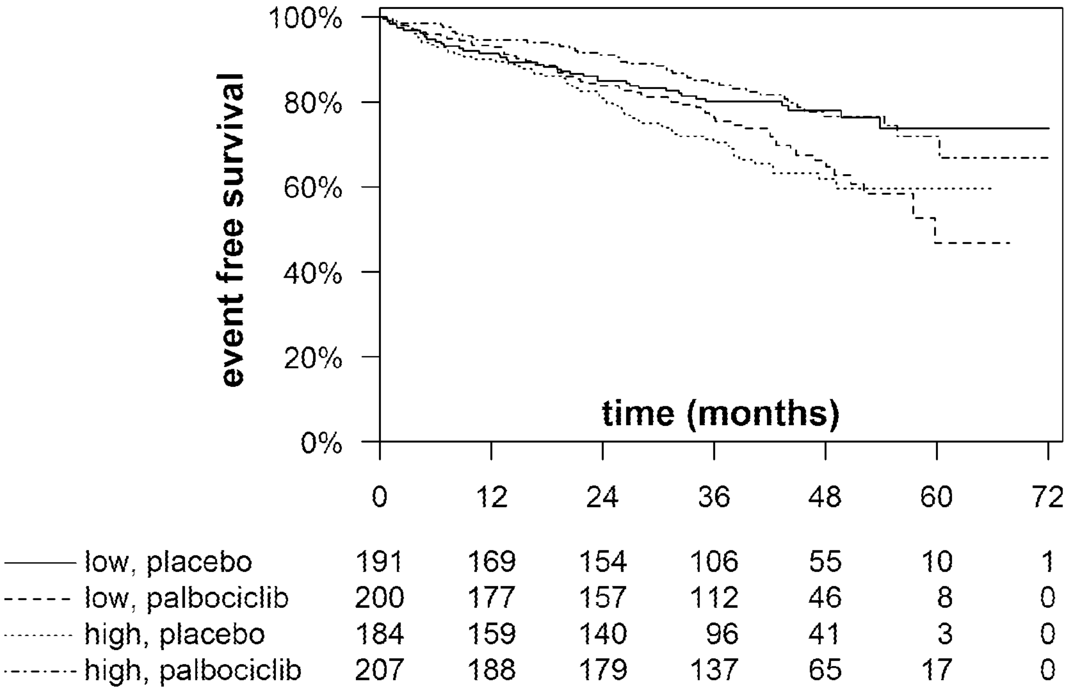
FIG. 3 shows a Kaplan-Meier plot for the "Signature 2" marker panel of Example 5.

After dichotomization of score2 at the median the Kaplan-Meier curves look similar as for score1; see FIG. 3.

Figure 5:
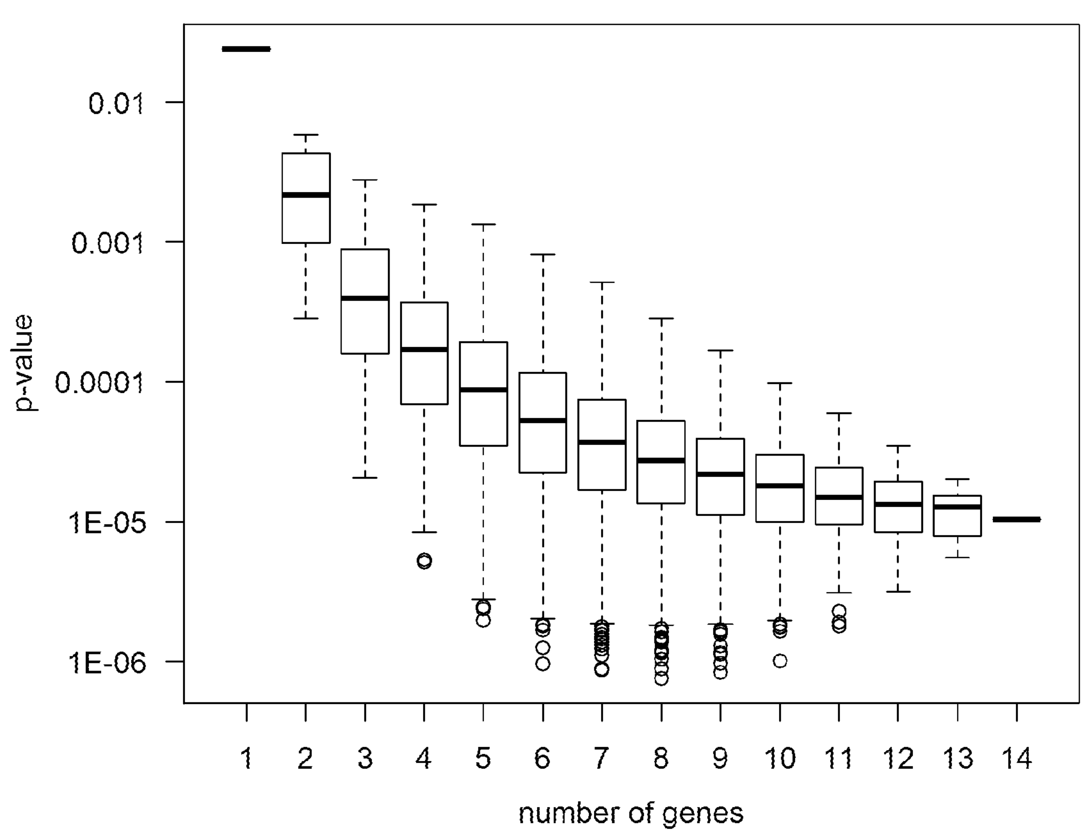
FIG. 5 shows a whisker-and-box plot for marker subsets from Signature 2 with the p-values of these interaction tests on the y-axis and the number of genes (i.e. subset size) on the x-axis.

FIG. 5 shows a whisker-and-box plot for Signature 2 with the p-values of these interaction tests on the y-axis and the number of genes (i.e. subset size) on the x-axis. In FIG. 5, box “1” contains CD274 (PD-L1) as a single gene; box “2” combines CD274 with each other gene from Signature2; and box “14” shows the one and only p-value for Signature2. Similar conclusions can be made: More genes result in smaller interaction p-values, but the gain of each gene decreases with the total number of genes in the subset.

The best (overfitted) subset consists of genes ABCA5, ABCB6, ABCC1, DSG3, MAP2K6, NF2, PIAS2, and CD274. When linearly combined using the coefficients of Signature2, Cox models results are shown in Table 19:

TABLE 19

| model | n | HR(in placebo, CI) | HR(in palbociclib, CI) | p |
|---|---|---|---|---|
| bivar | 782 | 1.30 (1.12-1.51) | 0.78 (0.69-0.89) | 7.61e–07 |
| multi1b | 770 | 1.30 (1.11-1.53) | 0.76 (0.66-0.88) | 7.058e–07 |
| multi2b | 782 | 1.31 (1.12-1.54) | 0.76 (0.67-0.87) | 2.542e–07 |

Example 6: Gene Replacements

Genes in Signature 1 and Signature 2 are not only correlated to each other, but also correlated to genes not used in Signature 1 or Signature 2. If some gene A from Signature1 is highly correlated to some gene B not in Signature 1, then gene A may be replaced by gene B in Signature 1 with only small (and clinically irrelevant) changes in the score value. When replacing gene A by gene B the expression values might be adjusted by an appropriate univariable transformation of the expression; examples for such a transformation may be:

- Univariable linear regression with the expression of gene B as dependent variable and gene A as independent variable. This procedure ensures minimal changes in score) among all affine linear transformations.
- If the correlation between A and B is positive, z-transformations for both may be calculated and the z-transformed expression values assumed to be equal. The result is a linear transformation composed from the z-transformation of B and the inverse z-transformation of A. This procedure preserves the mean and standard variation of score) among the cohort.
- One may not adjust any gene expression before calculating score) (which will result in different score) levels per patient), but adjust of the cutoff(s) applied to score) for clinical decision making instead. The new cutoff(s) may be determined by evaluating clinical variables, e.g. endpoints such as iDFS, DFS, RFI or OS.

Genes with a Pearson correlation coefficient of 0.7 or higher can be used as replacements for genes in Signature 1 or Signature 2. The following Table 20 shows potential replacement genes for the genes in Signature 1 or Signature 2 or the signature scores itself.

TABLE 20

| gene in Signature 1 and Signature 2 | potential replacement genes |
|---|---|
| ABCB6 | IL23A |
| ABCC12 | ABCC11 |
| CALML3 | ANXA8, TP63 |
| CCL13 | ABCB4, ABCB5, ABCG8, ACKR4, ACVR1C, ADAM23, ADORA2B, AICDA, AK3, ALK, ANG, ANGPT1, APCS, AQP2, AQP4, AQP9, AURKC, BCL2L10, BCL6, BLM, BMP5, BMP8B, CA9, CACNA1E, CASP1, CASP5, CCL1, CCL11, CCL17, CCL20, CCL23, CCL24, CCL26, CCL3, CCL7, CCL8, CCNA1, CCNH, CCR2, CCR3, CCR4, CCR6, CCR8, CCR9, CCRL2, CD160, CD209, CD274, CD28, CD33, CD40LG, CD80, CDH3, CDKL5, CDX2, CEACAM3, CEACAM7, CFTR, CKMT2, CNPY1, CNTF, COL4A3, COL4A4, CRLF2, CRP, CSF3, CTLA4, CXCL1, CXCL11, CXCL3, CXCL5, CXCL6, CXCL8, CXCR1, CXCR2, CXCR5, CXCR6, CYP19A1, CYP1A1, CYP1A2, CYP2C19, CYP2C9, CYP3A4, CYP3A5, DDX10, DEFB1, DHH, DLL3, DNAJB13, DNAJB7, DNAJC5B, DNAJC5G, DPPA2, DPPA3, DPPA4, DPPA5, EN2, EPO, EREG, ESRRB, ETV2, F8, FABP7, FAM133A, FAM64A, FASLG, FBXW7, FGF14, FGF16, FGF23, FGF6, FGF8, FGF9, FGFBP1, FLRT1, FMO3, GABBR2, GBP7, GDF3, GFAP, GNG4, GPR17, GRIN2A, GSTA2, GYS2, GZMB, GZMH, HHIP, HNF1B, HNF4A, HOXD1, HRK, HSPB3, IBSP, ICOS, IFNA2, IFNA5, IFNB1, IFNG, IFNW1, IGFBP1, IL11, IL12B, IL12RB2, IL13RA2, IL15, IL17A, IL17F, IL19, IL1A, IL1R2, IL2, IL20RB, IL21, IL22RA1, IL22RA2, IL23A, IL23R, IL24, IL2RA, IL3, IL5, IL7, IRGM, ISL1, ITGB3, ITLN2, KCNIP1, KL, KLB, KLF17, KLRD1, KNG1, KRT6A, LCN1, LEFTY1, LEFTY2, LIN28A, LIN28B, LIPE, LMO2, LRMP, LTA, LYN, LYVE1, MAGEA11, MAGEA2, MAGEA4, MAGEB1, MAGEB2, MAGEB3, MAGEC1, MAGEC2, MAOA, MBL2, MIXL1, MOS, MPL, MPO, MS4A1, MSH4, MSTN, MTCP1, MYCL, NCAM1, NEIL3, NGF, NLRP3, NOD2, NODAL, NOX1, NPPB, NR1H4, NR5A2, NRG3, NRG4, NTF3, OPCML, OR10J3, OTX2, PIK3CG, PLA2G4A, PLA2G5, PLG, PPARGC1A, PPBP, PPP2R2B, PRDM14, PRF1, PRKACG, PRKCB, PRL, PRMT8, PROK1, PROK2, PSG2, PTCHD1, PTCHD3, PTPN5, PTPRR, RAB6B, RAG1, RASAL1, RBPMS2, RND2, RSPO2, RUNX3, RXRG, S100A8, SCN1A, SERPINA9, SERPINB2, SERPINC1, SHC3, SLC10A1, SLC10A2, SLC22A2, SLC22A7, SLC22A8, SLC22A9, SLC25A4, SLC2A14, SLC3A1, SLCO1A2, SLCO1B3, SOX3, SPINK5, SSX1, STAT4, STK32A, T, TAL1, TBX21, TCL1A, TDGF1, TGFB2, TLR2, TLR8, TLR9, TLX1, TNFRSF8, TNFRSF9, TNFSF14, TNFSF15, TNFSF8, TNR, TP53AIP1, TSHR, TSLP, UGT1A1, UGT1A4, UGT1A6, UGT2B7, WNT16, WNT2B, WNT8A, WNT8B, XCL1, XCL2, XCR1, ZFP42 |
| DSG3 | ADORA2B, ALK, ANXA8, CA9, CCL8, CDC14B, CDH3, CYP2C19, DEFB1, DPPA2, DPPA3, FABP7, FGF6, FGFBP1, GDF3, IFNA5, IFNB1, IL1R2, IL20RB, ITLN2, KLK5, KRT16, KRT6A, PLG, POU5F1, SSX1, TAL1, TP63 |
| HPSE | ABCB4, ABCG8, ACVR1C, ADAM23, ADORA2B, AK3, ALK, APCS, AQP4, AQP9, BCL2A1, BCL2L10, BID, BLM, BMP8B, BTK, CA9, CACNA1E, CASP1, CASP5, CCL1, CCL11, CCL20, CCL23, CCL26, CCL3, CCL7, CCL8, CCR2, CCR3, CCR8, CCR9, CCRL2, CD160, CD209, CD274, CD28, CD33, CD40LG, CD80, CD86, CDC25A, CDC25C, CDH3, CEACAM7, CFTR, CNPY1, CNTF, COL4A3, CRP, CTSV, CXCL11, CXCL5, CXCL8, CYP19A1, CYP2C19, CYP2C9, DDX10, DEPDC1, DIAPH3, DNAJB13, DNAJB7, DNAJC5B, DNAJC5G, DPPA2, DPPA3, DPPA4, EPO, ETV7, FABP7, FAM133A, FAM64A, FASLG, FBXW7, FGF23, FGF6, FGFBP1, FMO3, GBP7, GDF3, GSTA2, GYS2, GZMA, GZMH, HAVCR2, HHIP, HOXD1, HRK, HSPB3, IBSP, ICOS, IFNA_Family, IFNA2, IFNA5, IFNB1, IFNG, IFNW1, IGFBP1, IL12RB2, IL13RA2, IL15, IL17A, IL17F, IL19, IL1A, IL2, IL20RB, IL21, IL22RA2, IL23A, IL23R, IL24, IL2RA, IL5, IL7, IRF5, IRGM, ISL1, ITLN2, KCNIP1, KLB, KLRD1, KNG1, KRT6A, LCN1, LIN28A, LIN28B, LIN9, LIPE, LMO2, LRMP, LTA, LYN, MAGEA2, MAGEB1, MAGEB3, MAGEC1, MAGEC2, MAOA, MBL2, MIXL1, MPL, MS4A1, MSTN, MTCP1, MYCL, NDC80, NEIL3, NOD2, NOX1, NPPB, NR1H4, NRG3, OR1013, OTX2, PIK3CG, PLA2G4A, PLG, POUSF1, PPBP, PPP2R2B, PRDM14, PRL, PROK1, PROK2, PSG2, PTCHD3, PTPN5, RAD51, RAG1, RASAL1, RND2, RSPO2, S100A8, SCN1A, SERPINA9, SERPINB2, |

TABLE 20-continued

| gene in Signature 1 and Signature 2 | potential replacement genes |
|---|---|
| | SERPINC1, SLC10A1, SLC10A2, SLC22A2, SLC22A9, SLC25A4, SLC7A7, SLCO1A2, SLCO1B3, SOX3, SPINK5, SSX1, STAT4, STK32A, TAL1, TDGF1, TGFB2, TLR2, TLR7, TLR8, TNFRSF9, TNFSF15, TNFSF8, TNR, TSHR, TSLP, TTK, UGT1A4, UGT1A6, UGT2B7, WNT16, WNT8A, XCL1, XCL2 |
| IL1RAP | ABCB4, ADAM23, ADORA2B, AK3, AQP4, AQP9, BCL2L10, CASP5, CCL1, CCL20, CCL26, CCL8, CD274, CD33, CD40LG, CD80, CDC14B, CDH3, CEACAM7, CXCL11, CXCL5, CXCL8, CYP19A1, CYP2C19, CYP2C9, DDX10, DNAJB7, DNAJC5G, DPPA2, DPPA3, DPPA4, FAM64A, FASLG, FBXW7, FGF14, FGFBP1, FMO3, GDF3, GSTA2, GYS2, HHIP, IFNA_Family, IFNA2, IFNA5, IFNW1, IGFBP1, IL13RA2, IL17A, IL2, IL20RB, IL21, IL22RA2, IL23R, IRF5, IRGM, ITLN2, KCNIP1, KLRD1, KNG1, LAMA1, LEFTY2, LRMP, LYN, MBL2, MPL, MS4A1, MSTN, NANOG, NAT2, NOX1, NOX4, NPPB, NR1H4, OR10J3, PIK3CG, PLA2G4A, PLG, PPP2R2B, PRL, PROK2, PSG2, PTCHD3, RAG1, RASAL1, RSPO2, S100A7A, SCN1A, SLC10A1, SLC10A2, SLC22A2, SLC22A9, SLCO1A2, SLCO1B3, TAL1, TDGF1, TGFB2, TLR2, TLR8, TNFRSF9, TNFSF8, TNR, TP63, TRAF6, TSHR, TSLP, UGT2B7, XCL1 |
| PEX12 | ABCB4, ABCB5, ABCG2, ABCG8, ACKR4, ACVR1C, ADAM23, ADORA2B, AHRR, AICDA, AK3, ALK, AMER1, ANGPT1, ANXA8, APCS, AQP2, AQP4, AQP7, AQP9, ASB9, ATP6V1G2, AURKC, BCL2L10, BCL6, BDNF, BLM, BMP5, BMP8B, BOD1, C19orf40, CA9, CACNA1E, CASP5, CCDC103, CCL1, CCL11, CCL15, CCL20, CCL23, CCL24, CCL26, CCL3, CCL7, CCL8, CCNH, CCR2, CCR3, CCR6, CCR8, CCR9, CCRL2, CCT6B, CD160, CD209, CD28, CD33, CD40LG, CD80, CDC14B, CDC25A, CDC25C, CDH13, CDH3, CDKL5, CEACAM3, CEACAM7, CFTR, CKMT2, CNPY1, CNTF, COL4A3, COL4A4, CRLF2, CRLS1, CRP, CSF3, CSNK1E, CXCL11, CXCL5, CXCL6, CXCL8, CXCR1, CXCR2, CYP19A1, CYP1A1, CYP1A2, CYP2C19, CYP2C8, CYP2C9, CYP2U1, CYP3A4, CYP3A5, DDX10, DIAPH3, DISP2, DKK4, DNAJB13, DNAJB7, DNAJC18, DNAJC5B, DNAJC5G, DPPA2, DPPA3, DPPA4, DPPA5, EN2, EPO, EPOR, ERCC4, ESRRB, ETV2, ETV4, EYA1, F8, FABP7, FAM133A, FAM64A, FASLG, FBXW7, FEN1, FGF14, FGF16, FGF23, FGF6, FGF9, FGFBP1, FLRT1, FMO3, GAB1, GABBR2, GBP7, GDF3, GNG4, GPR17, GPR180, GRIN2A, GSTA2, GYS2, GZMH, HHIP, HNF1B, HNF4A, HOXD1, HRK, HSPB3, IBSP, ICOS, IFNA_Family, IFNA2, IFNA5, IFNB1, IFNG, IFNW1, IGFBP1, IL11, IL12B, IL12RB2, IL13RA2, IL17A, IL17F, IL19, IL1A, IL2, IL20RB, IL21, IL22RA1, IL22RA2, IL23A, IL23R, IL24, IL3, IL5, IL7, IRF5, IRF6, IRGM, ISL1, ITLN2, KCNIP1, KLB, KLF17, KLK2, KLRD1, KNG1, KRT13, KRT6A, LAMA1, LCN1, LEFTY1, LEFTY2, LIN28A, LIN28B, LIN9, LINC00886, LIPE, LMO2, LRMP, LTA, LYN, MAGEA11, MAGEA2, MAGEA4, MAGEB1, MAGEB2, MAGEB3, MAGEC1, MAGEC2, MAGEL2, MAOA, MAP3K13, MBL2, MIXL1, MOS, MPL, MPO, MS4A1, MSH4, MSTN, MTCP1, MYCL, NANOG, NAT2, NCAM1, NEIL3, NODAL, NOX1, NOX4, NPPB, NR1H4, NR1I2, NR5A2, NRG3, NRG4, NTF3, OLIG2, OPCML, OR10J3, OTX2, PALB2, PHB, PIK3CB, PIK3CG, PLA2G4A, PLA2G5, PLG, POU5F1, PPARGC1B, PPBP, PPM1D, PPP2R2B, PRDM14, PRL, PRLR, PROK1, PROK2, PSG2, PTCHD1, PTCHD3, PTPN5, RAB6B, RAD51, RAG1, RASAL1, RBPMS2, RND2, RPA3, RPS6KA6, RSPO1, RSPO2, RXRG, S100A7A, S100A8, SALL4, SCN1A, SCN3A, SERPINA9, SERPINB2, SERPINC1, SHC3, SLC10A1, SLC10A2, SLC15A1, SLC22A2, SLC22A7, SLC22A8, SLC22A9, SLC25A4, SLC2A14, SLC7A9, SLCO1A2, SLCO1B3, SOX3, SPINK1, SPINK5, SSX1, STAT4, STK32A, STRADB, T, TAL1, TDGF1, TERF1, TGFB2, THPO, TLR2, TLR3, TLR7, TLR8, TLX1, TNFRSF17, TNFRSF9, TNFSF13B, TNFSF15, TNFSF8, TNR, TRAF6, TSHR, TSLP, UGT1A1, UGT1A4, UGT1A6, UGT2B7, WNT16, WNT2B, WNT8A, WNT8B, XCL1, XCL2, XRCC2, ZFP42, ZNF502 |
| PIAS2 | PIK3C3 |
| CD274 | ABCB4, ABCB5, ABCG8, ACVR1C, ADAM23, ADORA2B, AK3, ALK, ANGPT1, APCS, AQP4, AQP9, BCL2A1, BCL2L10, BLM, BTK, CARD11, CASP1, CASP5, CCL1, CCL11, CCL20, CCL23, CCL26, CCL3, CCL7, CCL8, CCR2, CCR3, CCR4, CCR7, CCR8, CCR9, CCRL2, CD160, CD209, CD28, CD33, CD40LG, CD80, CDC14B, CDC25A, CDH3, CDKL5, CEACAM7, CFTR, COL4A3, COL4A4, CRLF2, CRP, CTLA4, CXCL1, CXCL11, CXCL3, CXCL5, CXCL8, CXCR1, CXCR2, CXCR6, CYP19A1, CYP2C19, CYP2C9, CYP3A4, CYP3A5, DDX10, DNAJB7, DNAJC5G, DPPA2, DPPA3, DPPA4, EPOR, ETV7, FABP7, FAM133A, FASLG, FBXW7, FGF14, FGF23, FGF6, FGF9, FGFBP1, FMO3, GBP2, GBP7, GDF3, GSTA2, GYS2, GZMA, GZMB, GZMH, HHIP, HOXD1, HRK, HSPB3, ICOS, IFNA_Family, IFNA2, IFNA5, IFNB1, IFNG, IFNW1, IGFBP1, IL12RB2, IL13RA2, IL15, IL17A, IL17F, IL19, IL1A, IL1R2, IL2, IL21, IL22RA1, IL22RA2, IL23R, IL24, IL2RA, IL5, IL7, IRF5, IRGM, ISL1, ITLN2, KCNIP1, KLB, KLRD1, KLRG1, KNG1, LEFTY2, LIN28A, LIN28B, LIPE, LRMP, LTA, LYN, MAGEA2, MAGEB3, MAGEC1, MAGEC2, MBL2, MIXL1, MPL, MS4A1, MSTN, MTCP1, MYCL, NANOG, NAT2, NCAM1, NOD2, NODAL, NOX1, NPPB, NR1H4, NR5A2, NRG3, OPCML, OR10J3, PIK3CG, PLA2G4A, PLG, PPBP, PPP2R2B, PRDM14, PRF1, PRKCB, PRL, PROK1, PROK2, PSG2, PTCHD1, PTCHD3, PTPN5, RAG1, RASAL1, RND2, RSPO2, RUNX3, S100A8, SCN1A, SERPINA9, SERPINB2, SERPINC1, SLC10A1, SLC10A2, SLC22A2, SLC22A9, SLCO1A2, SLCO1B3, SOX3, SPINK5, STAT4, STK32A, TAL1, TBX21, TDGF1, TGFB2, TLR2, TLR7, TLR8, TNFRSF17, TNFRSF8, TNFRSF9, TNFSF15, TNFSF8, TNR, TSHR, TSLP, UGT1A1, UGT1A4, UGT1A6, UGT2B7, WNT16, XCL1, XCL2, XCR1 |

TABLE 20-continued

| gene in Signature 1 and Signature 2 | potential replacement genes |
|---|---|
| score1 (Signature1) | ABCB4, ABCB5, ABCG2, ABCG8, ACKR4, ACVR1C, ADAM23, ADORA2B, AHRR, AICDA, AK3, ALK, AMER1, ANG, ANGPT1, ANXA8, APCS, AQP2, AQP4, AQP7, AQP9, ASB9, ATG12, ATG13, ATP6V1G2, AURKB, AURKC, BCL2L10, BCL6, BDNF, BID, BIRC5, BLM, BMP5, BMP8B, BOD1, BRAF, BTC, BTK, C17orf53, C19orf40, CA9, CACNA1C, CACNA1E, CASP1, CASP14, CASP5, CASP9, CCDC103, CCL1, CCL11, CCL15, CCL20, CCL23, CCL24, CCL26, CCL3, CCL7, CCL8, CCNB2, CCNH, CCR2, CCR3, CCR4, CCR6, CCR8, CCR9, CCRL2, CCT6B, CD160, CD209, CD274, CD28, CD33, CD40LG, CD59, CD80, CDC14B, CDC25A, CDC25C, CDC7, CDH13, CDH3, CDK1, CDKL5, CDX2, CEACAM3, CEACAM7, CFTR, CHEK1, CKMT2, CMTM1, CNPY1, CNTF, COL4A3, COL4A4, CPT1C, CRLF2, CRLS1, CRP, CRTAC1, CSF3, CSNK1E, CTSV, CXCL1, CXCL11, CXCL3, CXCL5, CXCL6, CXCL8, CXCR1, CXCR2, CXCR5, CYP19A1, CYP1A1, CYP1A2, CYP2C19, CYP2C8, CYP2C9, CYP2U1, CYP3A4, CYP3A5, DAPL1, DDX10, DEFB1, DEPDC1, DIAPH3, DISP2, DKK4, DLL3, DMD, DNAJB13, DNAJB7, DNAJC18, DNAJC5B, DNAJC5G, DPPA2, DPPA3, DPPA4, DPPA5, DTX1, E2F3, EN2, EPO, EPOR, ERCC4, ESR2, ESRRB, ETV2, ETV4, ETV7, EYA1, F8, FABP7, FAM117B, FAM133A, FAM64A, FANCB, FASLG, FBXW7, FEN1, FGF12, FGF14, FGF16, FGF23, FGF6, FGF8, FGF9, FGFBP1, FLRT1, FMO3, FOXL2, FZD5, GAB1, GABBR2, GAL, GATA5, GBP7, GDF3, GFAP, GNG4, GNGT2, GPR17, GPR180, GRIN2A, GSTA2, GYS2, GZMH, HES5, HHIP, HNF1B, HNF4A, HOXA10, HOXA11, HOXD1, HRK, HSP90AA1, HSPA2, HSPB3, HSPBAP1, IBSP, ICOS, IFNA_Family, IFNA2, IFNA5, IFNB1, IFNG, IFNW1, IFRD1, IGFBP1, IL11, IL12B, IL12RB2, IL13RA2, IL15, IL17A, IL17F, IL19, IL1A, IL1R2, IL2, IL20RB, IL21, IL22RA1, IL22RA2, IL23A, IL23R, IL24, IL2RA, IL3, IL5, IL7, IRAK2, IRF5, IRF6, IRGM, ISL1, ITGB3, ITLN2, KCNIP1, KL, KLB, KLF17, KLK2, KLK5, KLRD1, KLRG1, KNG1, KRT13, KRT6A, LAMA1, LAMC3, LCN1, LEFTY1, LEFTY2, LIN28A, LIN28B, LIN9, LINC00886, LIPE, LMO2, LRMP, LTA, LYN, MAGEA11, MAGEA2, MAGEA4, MAGEB1, MAGEB2, MAGEB3, MAGEC1, MAGEC2, MAGEL2, MALT1, MAOA, MAP3K13, MBL2, MCM4, MECOM, MIXL1, MOS, MPL, MPO, MS4A1, MSH4, MSTN, MTCP1, MYCL, NANOG, NAT2, NCAM1, NDC80, NEIL3, NFE2L2, NGF, NKX2_5, NLRP3, NOD2, NODAL, NOX1, NOX4, NPPB, NR1H3, NR1H4, NR112, NR5A2, NRG3, NRG4, NTF3, OLIG2, OPCML, OR10J3, ORM2, OTX2, PAK1IP1, PAK3, PALB2, PAX5, PF4V1, PGF, PHB, PIK3CB, PIK3CG, PLA2G4A, PLA2G4E, PLA2G5, PLG, POLR2J, POU5F1, PPARGC1B, PPAT, PPBP, PPM1D, PPP2R2B, PRDM14, PRKACG, PRL, PRLR, PRMT8, PROK1, PROK2, PSG2, PTCHD1, PTCHD3, PTPN5, PTPRR, RAB6B, RAD51, RAG1, RASAL1, RBPMS2, RND2, RPA3, RPRM, RPS6KA6, RSPO1, RSPO2, RXRG, S100A7A, S100A8, SALL4, SCN1A, SCN3A, SERPINA9, SERPINB2, SERPINC1, SHC3, SHC4, SIRT4, SLC10A1, SLC10A2, SLC15A1, SLC22A2, SLC22A7, SLC22A8, SLC22A9, SLC25A4, SLC2A14, SLC3A1, SLC7A9, SLCO1A2, SLCO1B3, SOX15, SOX3, SPINK1, SPINK5, SSX1, STAT4, STK32A, STRADB, T, TAL1, TBX21, TDGF1, TERF1, TGFB2, THPO, TLR2, TLR3, TLR7, TLR8, TLR9, TLX1, TNFRSF17, TNFRSF8, TNFRSF9, TNFSF13B, TNFSF15, TNFSF8, TNR, TP53AIP1, TP63, TRAF6, TSHR, TSLP, TTK, TXNL4B, UBXN2A, UGT1A1, UGT1A4, UGT1A6, UGT2B7, WNT16, WNT2B, WNT8A, WNT8B, XCL1, XCL2, XCR1, XRCC6, ZFP42, ZNF502 |
| score2 (Signature2) | ABCB4, ABCB5, ABCG2, ABCG8, ACKR4, ACVR1C, ADAM23, ADORA2B, AHRR, AICDA, AK3, ALK, AMER1, ANG, ANGPT1, ANXA8, APCS, AQP2, AQP4, AQP7, AQP9, ASB9, ATG12, ATG13, ATP6V1G2, AURKB, AURKC, BCL2L10, BCL6, BDNF, BID, BIRC5, BLM, BMP5, BMP8B, BOD1, BTC, BTK, C17orf53, C19orf40, CA9, CACNA1C, CACNA1E, CASP1, CASP14, CASP5, CASP9, CCDC103, CCL1, CCL11, CCL15, CCL20, CCL23, CCL24, CCL26, CCL3, CCL7, CCL8, CCNB2, CCNH, CCR2, CCR3, CCR4, CCR6, CCR8, CCR9, CCRL2, CCT6B, CD160, CD209, CD274, CD28, CD33, CD40LG, CD59, CD80, CDC14B, CDC25A, CDC25C, CDC7, CDH13, CDH3, CDK1, CDKL5, CDX2, CEACAM3, CEACAM7, CFTR, CHEK1, CKMT2, CMTM1, CNPY1, CNTF, COL4A3, COL4A4, CPT1C, CREB5, CRLF2, CRLS1, CRP, CRTAC1, CRYAA, CSF3, CSNK1E, CTSV, CXCL1, CXCL11, CXCL3, CXCL5, CXCL6, CXCL8, CXCR1, CXCR2, CXCR5, CYP19A1, CYP1A1, CYP1A2, CYP2C19, CYP2C8, CYP2C9, CYP2U1, CYP3A4, CYP3A5, DAPL1, DDX10, DEFB1, DEPDC1, DIAPH3, DISP2, DKK4, DLL3, DMD, DNAJB13, DNAJB7, DNAJC18, DNAJC5B, DNAJC5G, DPPA2, DPPA3, DPPA4, DPPA5, DTX1, E2F3, EN2, EPO, EPOR, ERCC4, EREG, ESR2, ESRRB, ETV2, ETV4, ETV7, EYA1, F8, FABP7, FAM117B, FAM133A, FAM64A, FANCB, FASLG, FBXW7, FEN1, FGF1, FGF12, FGF14, FGF16, FGF23, FGF6, FGF8, FGF9, FGFBP1, FLRT1, FMO3, FOSL1, FOXL2, FZD5, GAB1, GABBR2, GAL, GATA5, GBP7, GDF3, GFAP, GLI1, GNG4, GNGT2, GPR17, GPR180, GRIN2A, GSTA2, GYS2, GZMA, GZMH, HAND1, HES5, HHIP, HNF1B, HNF4A, HOXA10, HOXA11, HOXD1, HRK, HSP90AA1, HSPA2, HSPB3, HSPBAP1, IBSP, ICOS, IFNA_Family, IFNA2, IFNA5, IFNB1, IFNG, IFNW1, IFRD1, IGFBP1, IL11, IL12B, IL12RB2, IL13RA2, IL15, IL17A, IL17F, IL19, IL1A, IL1R2, IL2, IL20RB, IL21, IL22RA1, IL22RA2, IL23A, IL23R, IL24, IL2RA, IL3, IL5, IL7, IRAK2, IRF5, IRF6, IRGM, ISL1, ITGB3, ITLN2, ITM2A, KCNIP1, KL, KLB, KLF17, KLK2, KLK5, KLRD1, KLRG1, KNG1, KRT13, KRT6A, LAMA1, LAMC3, LCN1, LECT1, LEFTY1, LEFTY2, LIN28A, LIN28B, LIN9, LINC00886, LIPE, LMO2, LRMP, LTA, LYN, MAGEA11, MAGEA2, MAGEA4, MAGEB1, MAGEB2, MAGEB3, MAGEC1, MAGEC2, MAGEL2, MALT1, MAOA, MAP3K13, MBL2, MCM4, |

TABLE 20-continued

| gene in Signature 1 and Signature 2 | potential replacement genes |
|---|---|
| | MECOM, MIXL1, MOS, MPL, MPO, MS4A1, MSH4, MSTN, MTCP1, MUTYH, MYCL, NANOG, NAT2, NCAM1, NDC80, NEIL3, NFE2L2, NFE2L3, NGF, NKD1, NKX2_5, NLRP3, NOD2, NODAL, NOX1, NOX4, NPM2, NPPB, NR1H3, NR1H4, NR112, NR5A2, NR6A1, NRG3, NRG4, NTF3, OLIG2, OPCML, OR10J3, ORM2, OTX2, PAK1IP1, PAK3, PALB2, PAX5, PF4V1, PGF, PHB, PIK3CB, PIK3CG, PITX2, PLA2G4A, PLA2G4E, PLA2G5, PLG, POLD4, POLR2J, POU5F1, PPARGC1A, PPARGC1B, PPAT, PPBP, PPM1D, PPP2R2B, PRDM14, PRKACG, PRL, PRLR, PRMT8, PROK1, PROK2, PSG2, PTCHD1, PTCHD3, PTPN5, PTPRR, RAB6B, RAD51, RAG1, RASAL1, RBPMS2, RND2, RPA3, RPRM, RPS6KA6, RSPO1, RSPO2, RXRG, S100A2, S100A7A, S100A8, SALL4, SCN1A, SCN3A, SERPINA9, SERPINB2, SERPINC1, SHC3, SHC4, SIRT4, SLC10A1, SLC10A2, SLC15A1, SLC22A2, SLC22A7, SLC22A8, SLC22A9, SLC25A4, SLC2A14, SLC3A1, SLC7A9, SLCO1A2, SLCO1B3, SOX15, SOX3, SPINK1, SPINK5, SSX1, STAT4, STK32A, STRADB, T, TAL1, TBX21, TDGF1, TERF1, TGFA, TGFB2, THPO, TLR2, TLR3, TLR7, TLR8, TLR9, TLX1, TNFRSF10C, TNFRSF17, TNFRSF8, TNFRSF9, TNFSF13B, TNFSF15, TNFSF8, TNR, TP53AIP1, TP63, TRAF6, TSHR, TSLP, TTK, TXNL4B, UBXN2A, UGT1A1, UGT1A4, UGT1A6, UGT2B7, WNT16, WNT2B, WNT8A, WNT8B, XCL1, XCL2, XCR1, XRCC6, ZFP42, ZNF502 |

For ABCA5, ABCC, MAP2K6, and NF2 no gene with a Pearson correlation coefficient was found. Nevertheless, also genes or sets of genes with smaller Pearson correlation coefficients than 0.7 may be used to replace genes in Signature 1 or Signature 2.

The invention claimed is:

1. A method for predicting a response or resistance to and/or a benefit from treatment with an inhibitor of cyclin-dependent kinases 4 optionally CDK4/6 inhibitor in a subject suffering from a neoplastic disease comprising:

determining in a sample obtained from said subject the expression level of at least one marker selected from the group consisting of Desmoglein 3 (DSG3), Intraflagellar Transport Protein 52 (IFT52), genes associated with multidrug resistance, and genes associated with SUMOylation, wherein the neoplastic disease is hormone receptor (HR)-positive, human epidermal growth factor receptor 2 (HER2)-negative breast cancer, wherein the genes associated with multidrug resistance are selected from the group consisting of ATP-binding Cassette Sub-Family B Member 6, mitochondrial (ABCB6), Multidrug resistance-associated protein 1 (ABCC1), ATP-binding Cassette Sub-family A Member 5 (ABCA5), ATP-binding Cassette Sub-family C Member 6 (ABCC6) and ATP-binding Cassette transporter Sub-family C Member 11 (ABCC11), ATP Binding Cassette Subfamily C Member 12 (ABCC12), and/or wherein the genes associated with SUMOylation are selected from the group consisting of Protein Inhibitor of Activated STAT 2 (PIAS2), Dual specificity mitogen-activated protein kinase kinase 6 (MAP2K6), Conserved Helix-Loop-Helix Ubiquitous Kinase (CHUK), Small ubiquitin-related modifier 1 (SUMO1), G/T mismatch-specific thymine DNA glycosylase (TDG), Inhibitor of Nuclear Factor Kappa-B Kinase Subunit gamma (IKBKG) and Xeroderma pigmentosum, complementation group C (XPC), wherein the expression level of the at least one marker is indicative for predicting the response or resistance to and/or the benefit from the treatment with the CDK4/6 inhibitor in said subject.

2. The method of claim 1, wherein the at least one marker is selected from the group consisting of PD-L1, PIAS2, MAP2K6, DSG3, ABCC12 and IFT52.

3. The method of claim 1, wherein a panel of two or more markers is determined, optionally at least two, three, four or five markers selected from the group consisting of, PIAS2, MAP2K6, DSG3, ABCC12 and IFT52 is determined in said sample.

4. The method of claim 1, wherein the method further comprises determining at least one marker selected from the group consisting of Programmed Death Ligand 1 (PD-L1), CALML3, CCL13, HPSE, IL1RAP, NF2, and PEX12.

5. The method of claim 1, wherein the method further comprises determining at least one marker selected from the group consisting of ABCA5, ABCB6, ABCC1, ABCC12, DSG3, MAP2K6, PIAS2, CALML3, CCL13, HPSE, IL1RAP, NF2, and PEX12.

6. The method of claim 1, wherein the is hormone receptor (HR)-positive, human epidermal growth factor receptor 2 (HER2)-negative breast cancer is either primary diagnosed or locally advanced or metastatic breast cancer.

7. The method of claim 1, wherein the CDK4/6 inhibitor is selected from the group consisting of palbociclib, ribociclib, abemaciclib and trilaciclib, optionally palbociclib.

8. The method of claim 1, wherein the sample is a tumor tissue sample, optionally wherein the sample is a primary tumor tissue sample, optionally a core biopsy sample, optionally a core biopsy sample from a primary tumor before any treatment.

9. The method of claim 7, wherein the sample is a post-surgical residual tumor tissue sample or a post-surgical lymph node sample, optionally a post-surgical and post-chemotherapy tissue sample.

10. The method of claim 1, wherein the expression level is determined at mRNA level in a hybridization-based method, a PCR based method, a microarray-based method, a sequencing and/or next generation sequencing method, or at protein level in an immunohistochemistry (IHC) assay.

11. A method of treating a neoplastic disease with an CDK4/6 inhibitor in a subject, wherein the subject has been determined to have a benefit from treatment with a CDK4/6 inhibitor in the method of claim 1, wherein the neoplastic disease is a hormone receptor (HR)-positive, human epidermal growth factor receptor 2 (HER2)-negative breast cancer.

12. A method of treating a neoplastic disease with an CDK4/6 inhibitor in a subject, wherein the subject has been determined to have an increased expression level of at least one marker selected from the group consisting of PIAS2, MAP2K6, DSG3, ABCC12, IFT52, ABCB6, ABCC1, ABCA5, ABCC6, ABCC11, CHUK, SUMO1, TDG, AURKA, SMC3 and IKBKG and/or an decreased expression level of XPC, in a sample of said subject, optionally wherein the CDK4/6 inhibitor is selected from the group consisting of palbociclib, ribociclib, abemaciclib and Trilaciclib, wherein the neoplastic disease is a hormone receptor (HR)-positive, human epidermal growth factor receptor 2 (HER2)-negative breast cancer.

13. The method of claim 1, wherein the method further comprises determining at least one marker selected from the group consisting of Programmed Death Ligand 1 (PD-L1), AURKA, and SMC3, wherein a higher expression level of PD-L1, PIAS2, MAP2K6, DSG3, IFT52, ABCB6, ABCC1, ABCA5, ABCC6, ABCC11, ABCC12, CHUK, SUMO1, TDG, AURKA, SMC3 and IKBKG, is associated with a higher likelihood of benefit from the CDK4/6 inhibitor, and a lower expression is associated with a lower benefit, no benefit or a disadvantage from the CDK4/6 inhibitor.

14. The method of claim 1, wherein at least two, three, four, five, six, seven, eight, nine, ten, eleven, twelve, or thirteen markers are selected.

* * * * *